(12) United States Patent
Drake et al.

(10) Patent No.: US 7,018,834 B2
(45) Date of Patent: Mar. 28, 2006

(54) MUTATED HERPES SIMPLEX VIRUS TYPE 1 THYMIDINE KINASES AND USES THEREOF

(75) Inventors: Richard Drake, Little Rock, AR (US);
Trenton Hinds, Portsmouth Commonwealth (DM); Cesar Compadre, Little Rock, AR (US);
Barry Hurlburt, Little Rock, AR (US);
Tammy Rechtin, Birmingham, AL (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 197 days.

(21) Appl. No.: 10/457,604

(22) Filed: Jun. 9, 2003

(65) Prior Publication Data

US 2003/0202964 A1    Oct. 30, 2003

Related U.S. Application Data

(62) Division of application No. 09/877,381, filed on Jun. 8, 2001, now Pat. No. 6,610,289, which is a division of application No. 09/338,308, filed on Jun. 22, 1999, now Pat. No. 6,245,543.

(60) Provisional application No. 60/090,271, filed on Jun. 22, 1998.

(51) Int. Cl.
*C12N 15/63* (2006.01)

(52) U.S. Cl. .................................. 435/320.1; 435/325

(58) Field of Classification Search ............. 435/320.1, 435/325

See application file for complete search history.

Primary Examiner—Celine Qian
(74) Attorney, Agent, or Firm—Benjamin Aaron Adler

(57) ABSTRACT

The present invention provides new site-specific HSV-thymidine kinase mutants with improved nucleoside analog metabolizing activity due to low or no thymidine phosphorylation ability. Also provided is a method of killing target cells using such mutants combined with a prodrug.

5 Claims, 15 Drawing Sheets

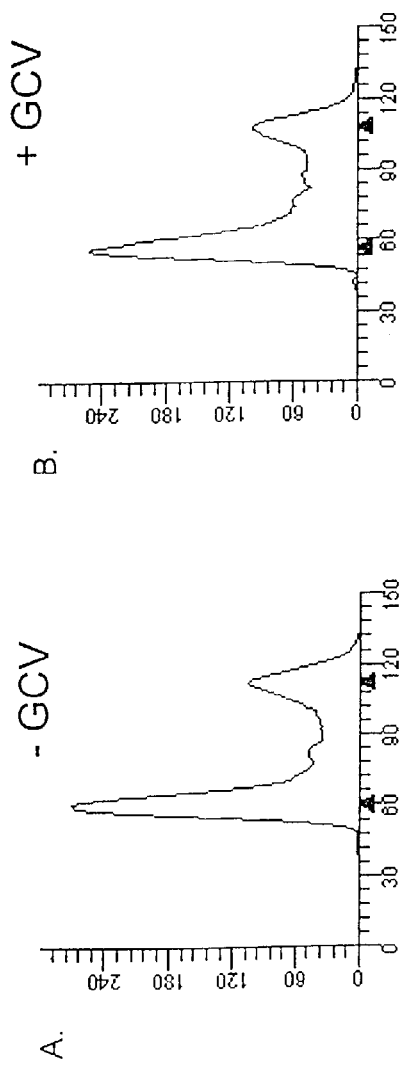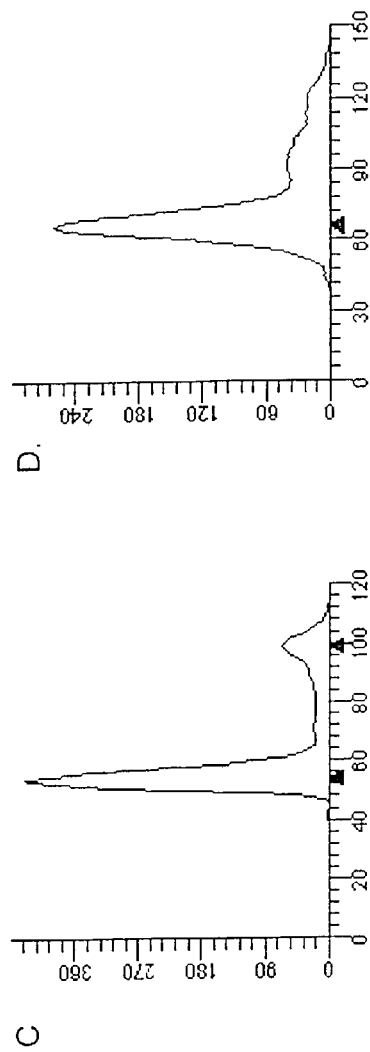

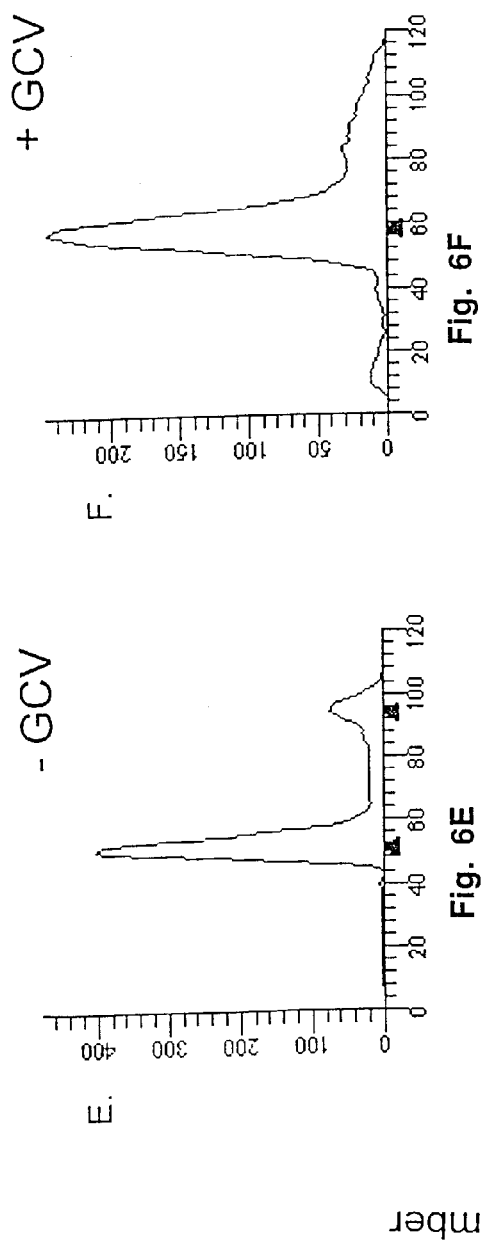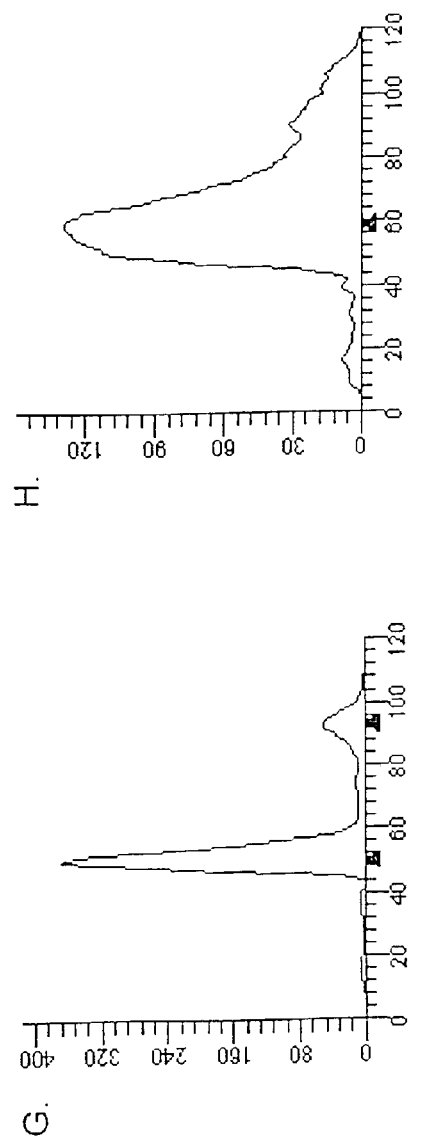

116WT-TK
Ctrl
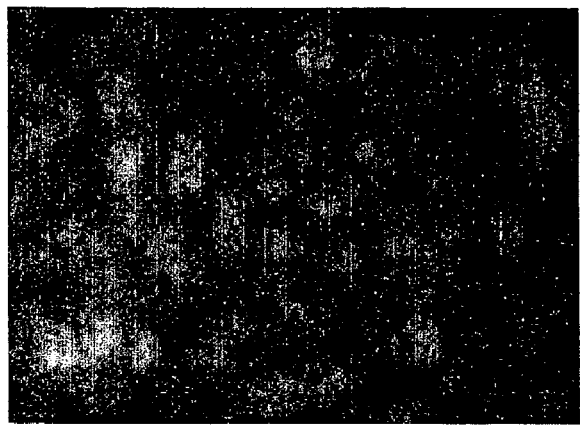
36hr
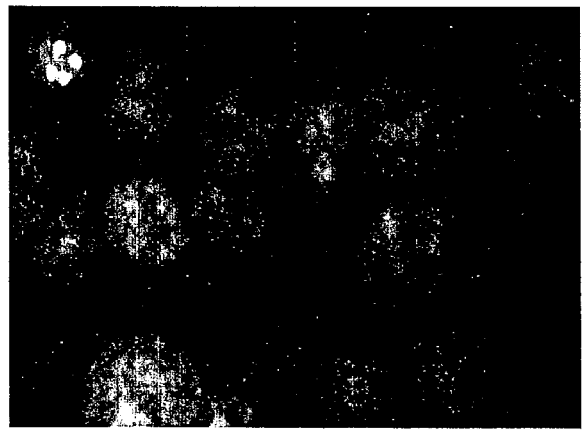
84hr
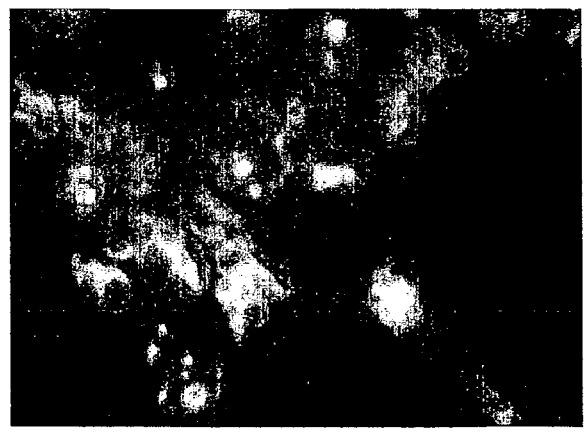
Fig. 7A

116Asn-TK
Ctrl
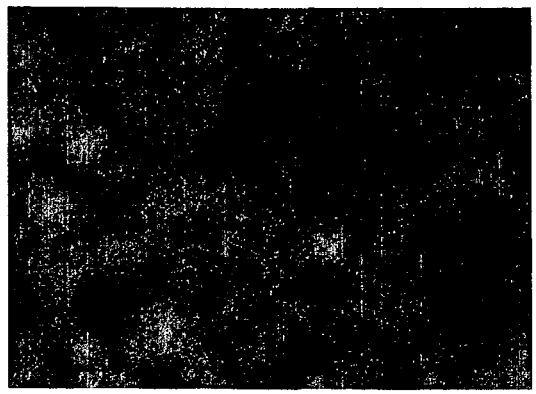
36hr
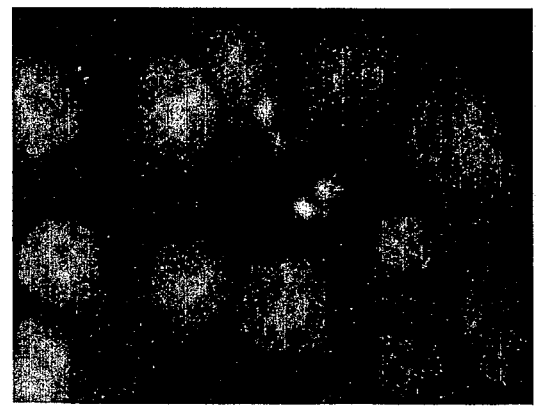
84hr
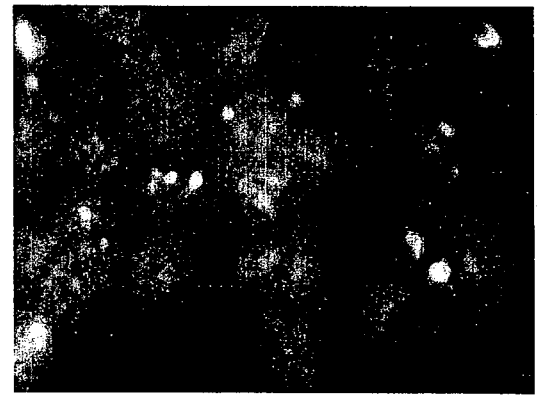
Fig. 7B

116Glu-TK
Ctrl
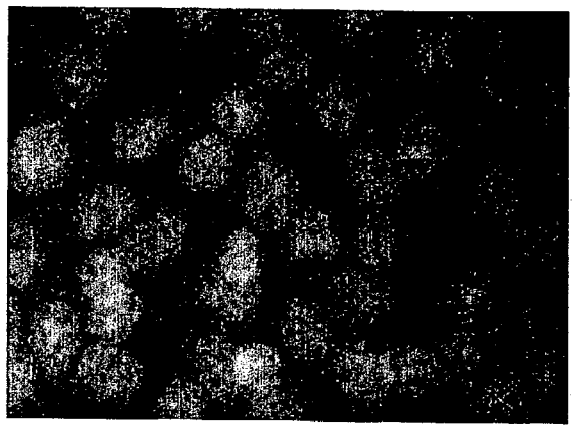
36hr
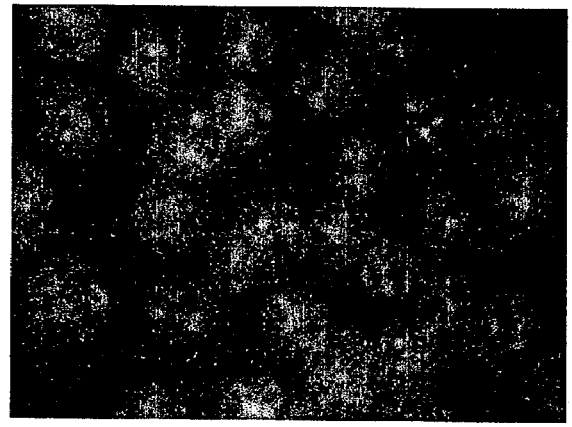
84hr
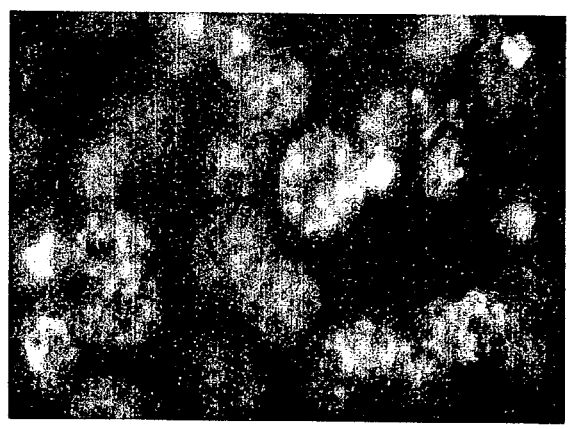
Fig. 7C

SEQUENCE LISTING

<160> NUMBER OF SEQ ID NOS: 4

<210> SEQ ID NO 1
<211> LENGTH: 21
<212> TYPE: DNA
<213> ORGANISM: artificial sequence
<220> FEATURE:
<221> NAME/KEY: primer_bind
<223> OTHER INFORMATION: a mutagenic oligonucleotide primer used to
      replace Gln-125 with Asp-125

<400> SEQUENCE: 1
acaagcgccg acataacaat g                                          21

<210> SEQ ID NO 2
<211> LENGTH: 21
<212> TYPE: DNA
<213> ORGANISM: artificial sequence

```
-continued

<220> FEATURE:
<221> NAME/KEY: primer_bind
<223> OTHER INFORMATION: a mutagenic oligonucleotide primer used to
      replace Gln-125 with Asn-125

<400> SEQUENCE: 2
acaagcgcca acataacaat g                                              21

<210> SEQ ID NO 3
<211> LENGTH: 21
<212> TYPE: DNA
<213> ORGANISM: artificial sequence
<220> FEATURE:
<221> NAME/KEY: primer_bind
<223> OTHER INFORMATION: a mutagenic oligonucleotide primer used to
      replace Gln-125 with Glu-125

<400> SEQUENCE: 3
acaagcgccg aaataacaat g                                              21

<210> SEQ ID NO 4
<211> LENGTH: 4
<212> TYPE: PRT
<213> ORGANISM: artificial sequence
<220> FEATURE:
<223> OTHER INFORMATION: a peptide substrate used for a colorimetric
      assay

<400> SEQUENCE: 4

Asp Val Glu Asp
```

MUTATED HERPES SIMPLEX VIRUS TYPE 1 THYMIDINE KINASES AND USES THEREOF

CROSS-REFERENCE TO RELATED APPLICATION

This is a divisional application of U.S. Ser. No. 09/877,381 filed on Jun. 8, 2001, now U.S. Pat. No. 6,610,289 which is a divisional of U.S. Ser. No. 09/338,308, filed on Jun. 22, 1999, now issued as U.S. Pat. No. 6,245,543.

This patent application claims benefit of provisional patent application U.S. Ser. No. 60/090,271, filed Jun. 22, 1998, now abandoned.

BACKGROUND OF THE INVENTION

1. Field of the Invention

The present invention relates generally to the field of molecular biology of herpes simplex viruses and vaccine technology. More specifically, the present invention relates to a means of improving gene therapy for diseases such as cancer by mutating herpes simplex virus type 1 thymidine kinases and uses thereof.

2. Description of the Related Art

The herpes simplex virus thymidine kinases (HSV-TKs)[1] are the pharmacological targets of most herpesvirus treatments (1,2), and more recently, HSV-1 TK has been utilized as a suicide gene therapeutic for cancer in combination with ganciclovir (3,4). The basis for these uses is their ability to specifically phosphorylate anti-herpesvirus nucleoside drugs such as acyclovir (ACV), ganciclovir (GCV) and 5-bromovinyldeoxyuridine (BVDU) (1,2,5). This targeting is based primarily on the differences in substrate specificity compared to the cellular TKs. The HSV-1 TK has a much broader range of substrates which include most pyrimidine nucleosides, many guanosine derivatives (e.g., ACV or GCV), and most purine and pyrimidine nucleoside triphosphates (6–9). HSV-TK also possesses a thymidylate kinase (TMPK) activity, but this activity is restricted to only deoxypyrimidine monophosphate substrates (7–9).

Proteolytic mapping studies of HSV-1 TK with the photoactive TMP analog, [$^{32}$P]5N$_3$dUMP, identified a region of the thymine base binding site inclusive in the peptide Ile$^{112}$-Tyr$^{132}$ (10). This report, and others (7,8,11,12), concluded that the thymine base of TMP and thymidine bind in one shared site. This was subsequently confirmed in comparisons of two X-ray crystal structures of HSV-1 TK with bound thymidine or TMP (13, 14). Two initial X-ray crystal structures of HSV-1 TK have been published (13,14), one with bound thymidine or ganciclovir (13) and the other with thymidine, 5-iodo-deoxyuridine monophosphate or a complex with TMP and ADP (14). Subsequent structures have been reported with bound acyclovir, penciclovir and other nucleoside drug substrates and inhibitors (15,16). Within the pyrimidine base binding site, all structures have indicated that hydrogen bonding between Gln-125 of HSV-1 TK and the N3 and O4 atoms of the pyrimidine base was evident (13–15). In the complex with ganciclovir or acyclovir, Gln-125 was shown to form hydrogen bonds with the N1 and O6 atoms of the guanine base of GCV (13,15,16).

The prior art is deficient in lack of improved mutants of herpes simplex virus type 1 thymidine kinases useful in treating cancers in gene therapy techniques so as to maximize therapeutic efficacy and minimize untoward side effects. Increasing and/or modifying the desired substrate specificity for HSV-thymidine kinase would ameliorate these side effects. The present invention fulfills this long-standing need and desire in the art.

SUMMARY OF THE INVENTION

It has been reported that site-directed mutagenesis of Gln-125 to Glu, Leu or Asn can modulate the substrate affinities for thymidine and ACV in the context of HSV-1 TK in antiviral drug resistance (17). To examine the role of Gln-125 in HSV-1 TK activity in the context of gene therapeutic applications, three separate site-specific mutations were made of this residue to either an Asp, Asn or Glu acid residue. These three mutants and wild-type HSV-1 TK were expressed in *E. coli,* partially purified, and then were compared for their ability to phosphorylate deoxypyrimidine and acyclic purine substrates. For each mutation, the ability to phosphorylate deoxypyrimidine substrates were greatly modified, while activity for the acyclic purines was variable. Kinetic constants for thymidine and GCV were also determined. The molecular basis for the obtained results were evaluated using Flexidock molecular modeling simulations of the different enzyme active sites. The genes for each mutant HSV-1 TK were incorporated into a retroviral plasmid for expression in two mammalian cell lines and evaluation of sensitivity to GCV killing. The potential uses of these mutants in gene therapy applications and in the design of new HSV-1 TK proteins with different activities is discussed.

In one embodiment of the present invention, there is provided a mutant herpes simplex virus type 1 thymidine kinase protein with a site-specific mutation at amino acid position 125 of wild type herpes simplex virus type 1 thymidine kinase.

In another embodiment of the present invention, there is provided a vector comprising a DNA sequence coding for the mutant herpes simplex virus type 1 thymidine kinase protein disclosed herein, a promoter and optionally an origin of replication.

In still another embodiment of the present invention, there is provided a host cell transfected with the above disclosed vector.

In still yet another embodiment of the present invention, there is provided a method of killing target cells, comprising the steps of transfecting or transducing the target cells with a gene encoding a non-human mutant herpes simplex virus type 1 thymidine kinase and then contacting the transfected or transduced cells with an effective amount of a prodrug, wherein the prodrug is a substrate for the mutant herpes simplex virus type 1 thymidine kinase to yield a toxic substance, which inhibits cellular DNA polymerases and kills the transfected or transduced target cells.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 3 shows sensitivity to GCV killing of wild-type and mutant HSV-1 TK expressing HCT-116 and NIH3T3 cell lines. HCT-116 and NIH3T3 cell lines stably expressed wild-type or mutant HSV-1 TKs under control of a Moloney murine leukemia virus promoter. Cells were plated in triplicate and exposed to 0, 0.05, 0.5 or 5 µM GCV for four days. Cell viabilities were determined using MTT dye. Results are presented as percent of untreated cell controls for each cell line.

FIG. 6 shows cell cycle analysis of GCV treated cells. Parental HCT-116 cells and each HSV-1 TK expressing cell line were grown to 60% confluency in 25 cm$^2$ flasks and treated for 24 hours minus (−GCV, panels A, C, E and G) or plus (+GCV, panels B, D, F and H) 25 µM GCV. Cells were fixed in 70% ethanol overnight, and later incubated with RNAase (0.1%) and propidium iodide (1 mg/ml) for 20 minutes on ice. Flow cytometry measuring propidium iodide fluorescence was done with a Becton-Dickinson FACScalibur instrument using MODFIT computer software. FIGS. 6A and 6B: HCT-116 cells; FIGS. 6C and 6D: wild-type HSV-1 TK cells; FIGS. 6E and 6F: Asn-125TK cells, FIGS. 6G and 6H: Glu-125TK cells.

FIG. 7 shows GCV-induced apoptosis in HSV-TK-expressing cell lines. The HCT-116 cells expressing wild-type HSV-1 TK (FIG. 7A), Asn-125TK (FIG. 7B), or Glu-125TK (FIG. 7C) were grown on chamber slides and incubated with 25 µM GCV for 36 or 84 hours. Control cultures for each cell line without GCV addition (top row) were evaluated after 84 hours. At the indicated time point, cells were fixed in methanol, stained with DAPI, and nuclei visualized by fluorescent microscopy. Each image is magnified 40×.

DETAILED DESCRIPTION OF THE INVENTION

Figure 1:
FIG. 1 shows autoradiograph of photolabeled wild-type and mutant HSV-1 TKs. Partially, purified extracts from each HSV-1 TK were photolabeled with the TMP photoaffinity analog, [$^{32}$P]5-azido-dUMP. Photolabeled proteins were separated on 10% SDS-polyacrylamide gels followed by autoradiography of the dried gel.
Figure 2A:
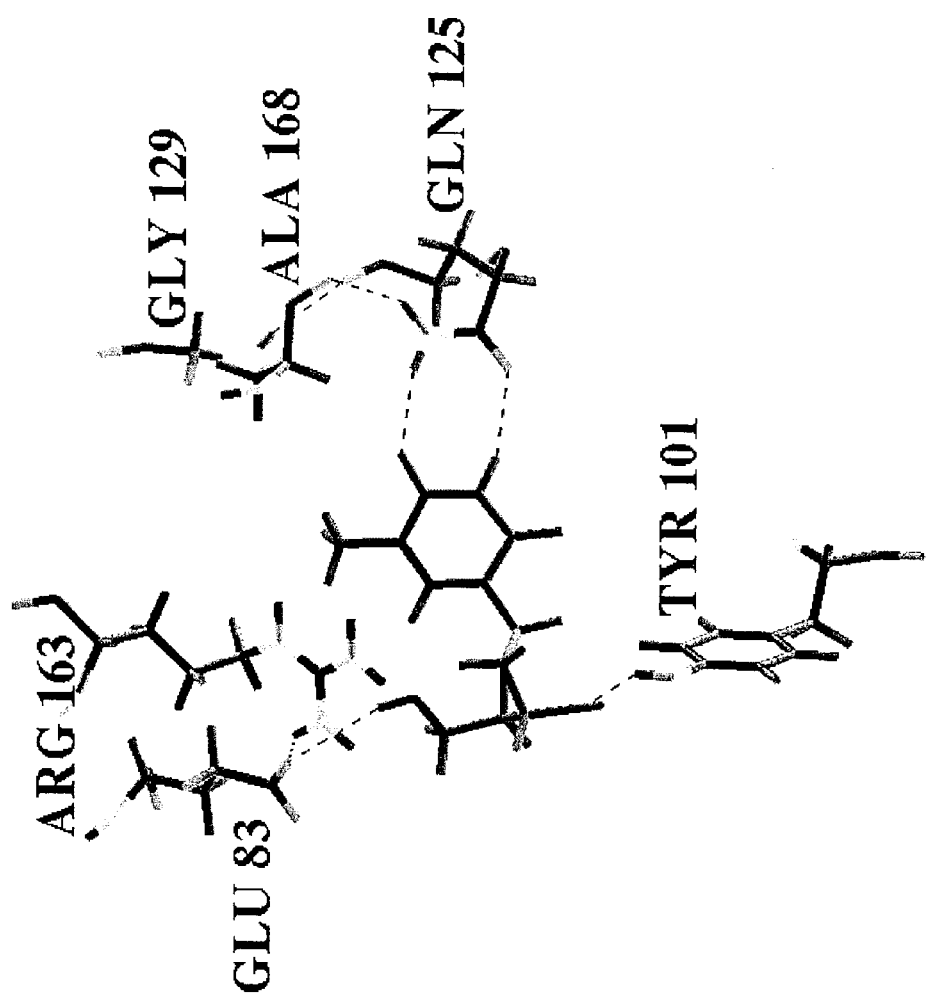
FIG. 2 shows Flexidock modeling of hydrogen bonding between thymine and amino acid 125. The Flexidock module of SYBL 6.3 was used to generate the lowest energy conformations of bound thymidine with wild-type Gln-125 HSV-TK (FIG. 2A), or the mutant HSV-1 TKs, Glu-125 (FIG. 2B), Asp-125 (FIG. 2C) or Asn-125 (FIG. 2D).
Figure 2B:
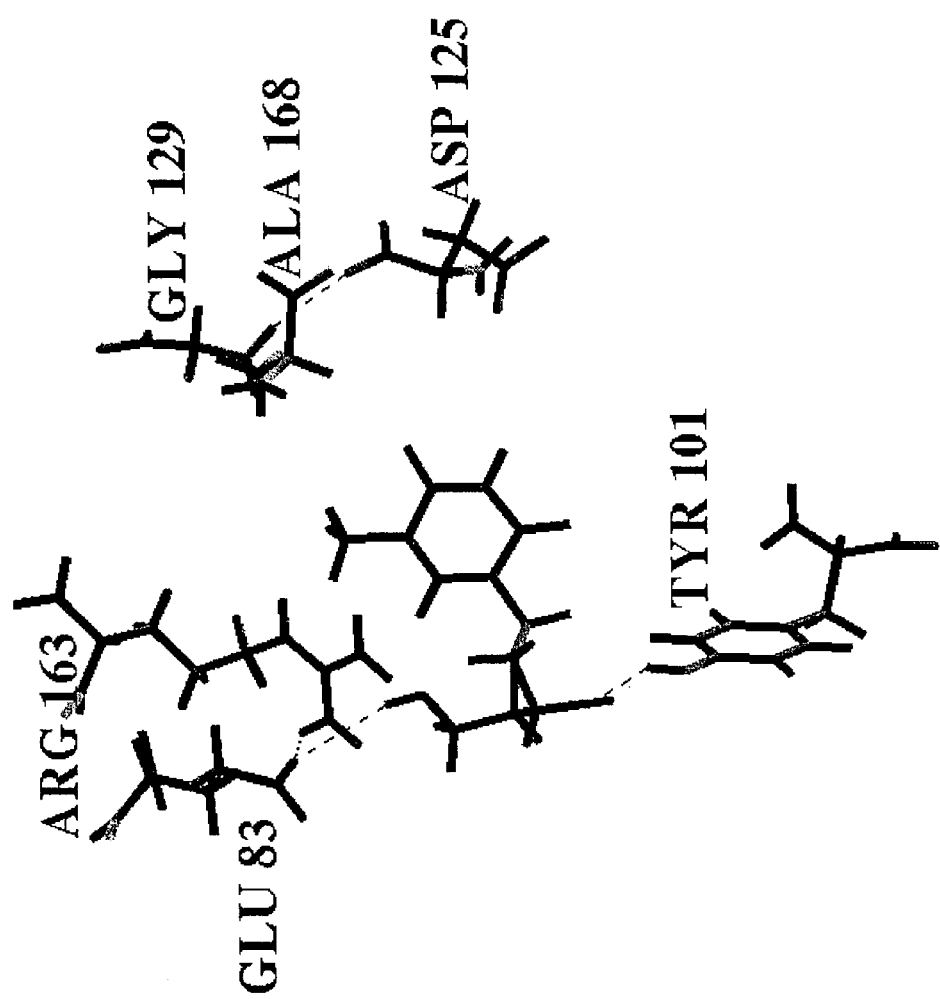
Figure 2C:
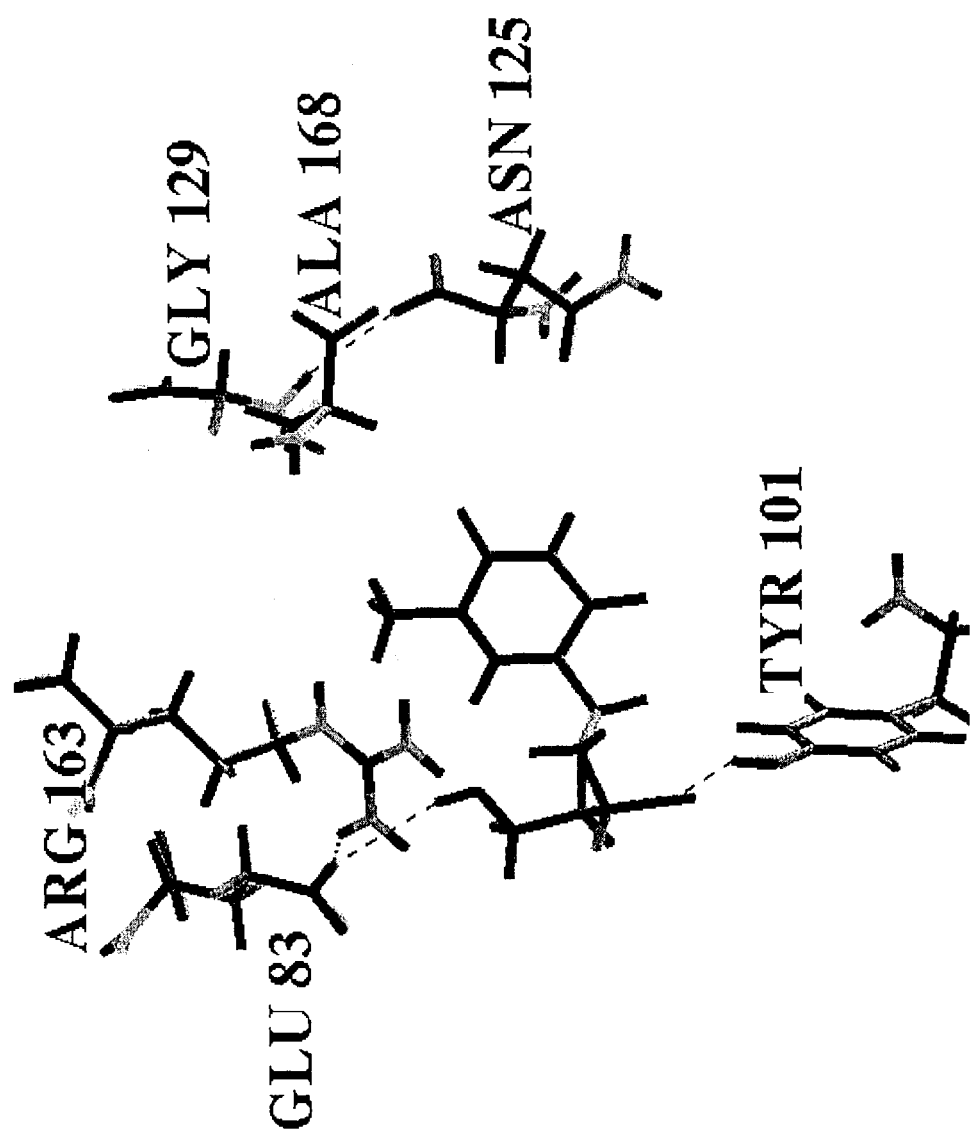
Figure 2D:
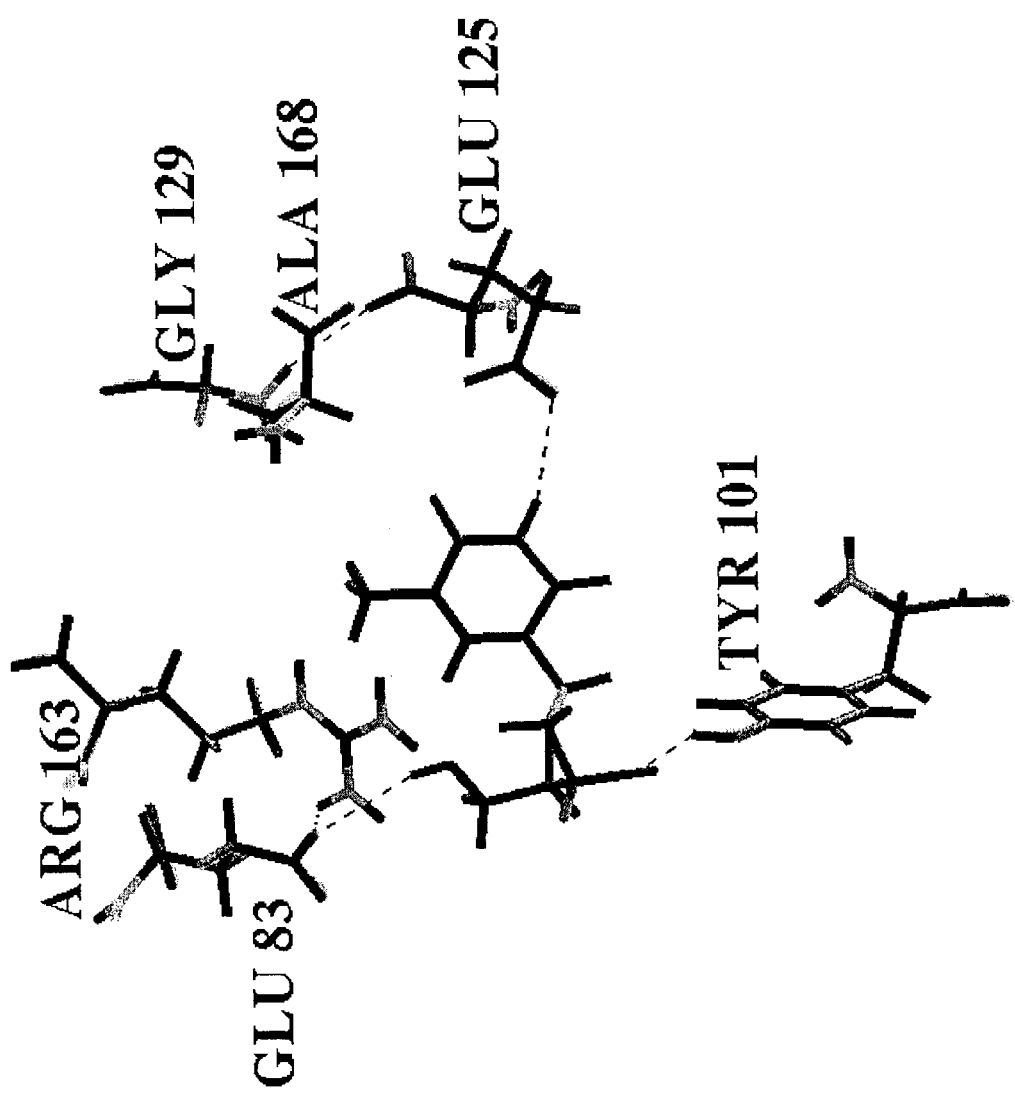

The herpes simplex virus type-1 thymidine kinase (HSV-1 TK) is the major anti-herpesvirus pharmacological target, and it is being utilized in combination with the prodrug, ganciclovir, as a suicide gene therapeutic for cancer. One active-site amino acid, glutamine-125 (Gln-125), has been shown to form hydrogen bonds with bound thymidine, thymidylate and ganciclovir in multiple X-ray crystal structures. To examine the role of Gln-125 in HSV-1 TK activity, three site-specific mutations of this residue to either an aspartic acid, asparagine or glutamic acid were introduced. These three mutants and wild-type HSV-1 TK were expressed in E. coli, partially purified, and their enzymatic properties compared. In comparison to the Gln-125 HSV-1 TK, TMPK activity was abolished in all three mutants. For thymidine kinase activity relative to Gln-125 enzyme, the $K_n$ of thymidine increased from 0.9 µM for the parent Gln-125 enzyme to 3 µM for the Glu-125 mutant, to 6000 µM for the Asp-125 mutant and to 20 µM in the Asn-125 mutant. In contrast, the $K_m$ of ganciclovir decreased from 69 µM for the parent Gln-125 enzyme to 50 µM for the Asn-125 mutant, and increased to 473 µM for the Glu-125 mutant. The Asp-125 enzyme was able to poorly phosphorylate ganciclovir, but with non-linear kinetics. Molecular simulations of the wild-type and mutant HSV-1 TK active-sites predict that the observed activities are due to loss of hydrogen bonding between thymidine and the mutant amino acids, while the potential for hydrogen bonding remains intact for ganciclovir binding. When expressed in two mammalian cell lines, the Glu-125 mutant led to GCV mediated killing of one cell line, while the Asn-125 mutant was equally effective as wild-type HSV-1 TK in metabolizing GCV and causing cell death in both cell lines.

The method of treatment basically consists of providing to target cells the mutant herpes simplex virus type 1 thymidine kinase gene and then exposing the cells to an appropriate substrate which is converted to a toxic substance to kill those cells expressing the mutant HSV-1 thymidine kinase gene as well as those in the vicinity of the mutant HSV-1 thymidine kinase gene-expressing cells, i.e., bystander cells. The mutant HSV-1 thymidine kinase gene can be administered directly to the targeted cells or systemically in combination with a targeting means, such as through the selection of a particular viral vector or delivery formulation. Cells can be treated in vivo, within the patient to be treated, or treated in vitro, then injected into the patient. Following introduction of the mutant HSV-1 thymidine kinase gene into cells in the patient, the prodrug is administered, systemically or locally, in an effective amount to be converted by the mutant HSV-1 thymidine kinase into a sufficient amount of toxic substance to kill the targeted cells. A nucleoside analog which is a substrate for HSV-1 TK to produce a toxic substance which kills target cells is referred to herein as a "prodrug".

The destruction of selected populations of cells can be achieved by targeting the delivery of the mutant HSV-1 thymidine kinase gene. The natural tropism or physiology of viral vectors can be exploited as a means of targeting specific cell types. For example, retroviruses are well known to become fully active only in replicating cells. This fact has been used as the basis for selective retroviral-mediated gene transfer to replicating cancer cells growing within a site where the normal (nonmalignant) cells are not replicating, in both animal and human clinical studies. Alternatively, the viral vector can be directly administered to a specific site such as a solid tumor, where the vast majority of the gene transfer will occur relative to the surrounding tissues. This concept of selective delivery has been demonstrated in the delivery of genes to tumors in mice by adenovirus vectors. Molecular conjugates can be developed so that the receptor binding ligand will bind only to selective cell types, as has been demonstrated for the lectin-mediated targeting of lung cancer.

Recently, it was shown that intravenous injection of liposomes carrying DNA can mediate targeted expression of genes in certain cell types. Targeting of a gene encoding a mutant HSV-1 thymidine kinase or expression of the gene to a small fraction of the cells in a tumor mass followed by substrate administration could be adequate to mediate involution.

Another example of protein delivery to specific targets is that achieved with liposomes. Methods for producing liposomes are described (e.g., Liposomes: A Practical Approach). Liposomes can be targeted to specific sites by the inclusion of specific ligands or antibodies in their exterior surface, e.g. targeting of specific liver cell populations by inclusion of asialofetuin in the liposomal surface (43). Specific liposomal formulations can also achieve targeted delivery, as best exemplified by the so-called Stealth' liposomes that preferentially deliver drugs to implanted tumors (44). After the liposomes have been injected or implanted, unbound liposome is allowed to be cleared from the blood, and the patient is treated with the prodrug. Again, this procedure requires only the availability of an appropriate targeting vehicle.

The present invention is directed to a novel means of improving upon the safety and efficacy of gene therapy, particularly for neoplastic disease. The invention provides mutant herpes simplex virus type 1 thymidine kinase proteins for use in gene therapy for cancer and viral diseases.

In one embodiment of the present invention, there is provided a mutant herpes simplex virus type 1 thymidine kinase protein, which contains a site-specific mutation at the amino acid position 125, i.e., glutamine residue of the wild type herpes simplex virus type 1 thymidine kinase protein. Preferably, the glutamine residue is mutated to a nonglutamine residue selected from the group consisting of glutamic acid, aspartic acid and asparagine.

The mutant herpes simplex virus type 1 thymidine kinase proteins of the present invention provide for improved metabolizing activity of nucleoside analogs such as ganciclovir, due to low or no endogenous thymidine phosphorylation ability, leading to enhanced therapeutic efficacy of the analogs.

The present invention is also directed to a vector comprising a DNA sequence coding for the mutant herpes simplex virus type 1 thymidine kinase protein disclosed herein and the vector is capable of replication in a host which comprises, in operable linkage: a) optionally, an origin of replication; b) a promoter; and c) a DNA sequence coding for the mutant protein. Preferably, the vector is selected from the group consisting of a retroviral vector, an adenoviral vector, an adeno-associated viral vector, a herpes vector, a viral vector and a plasmid.

The present invention is also directed to a host cell transfected with the vector of the present invention so that the vector expresses a mutant herpes simplex virus type 1 thymidine kinase protein. Preferably, such host cells are selected from the group consisting of bacterial cells, mammalian cells and insect cells.

In another embodiment of the present invention, there is provided a method of killing target cells in an individual in need of such treatment, comprising the steps of transfecting or transducing the target cells with a gene encoding a mutant herpes simplex virus type 1 thymidine kinase and then contacting the transfected or transduced cells with an effective amount of a prodrug, wherein the prodrug is a substrate for the mutant herpes simplex virus type 1 thymidine kinase and may be administered systemically or locally. The substrate is non-toxic to the target cells and is phosphorylated by the kinase to yield a toxic substance which inhibits cellular DNA polymerases and kills the transfected or transduced target cells. Representative examples of the prodrugs are nucleoside analogs acyclovir, ganciclovir and 5-bromovinyldeoxyuridine. Preferably, the targeted cells are selected from the group consisting of tumor cells and virally infected cells.

The following examples are given for the purpose of illustrating various embodiments of the invention and are not meant to limit the present invention in any fashion.

EXAMPLE 1

Materials

All reagents and nucleotides were purchased from Sigma Chemical Co. unless otherwise indicated. [$^3$H-methyl]thymidine (71 Ci/mmol), [$^3$H-methyl]AZT (19 Ci/mmol), [8-$^3$H]ganciclovir (17 Ci/mmol) and [8-$^3$H]acyclovir (15 Ci/mmol) were purchased from Moravek Biochemicals. [5-$^3$H]deoxycytidine (20 Ci/mmol) was from American Radiolabeled Chemicals. [γ-$^{32}$P]ATP was from ICN Radiochemicals. Whatman DE81 filter paper discs and DE-52 resin were purchased from Fisher. Automated DNA sequencing of plasmids was done by the U.A.M.S. Molecular Resource Laboratory using a Model 377 DNA Sequencer from Applied Biosystems. Oligonucleotide primers were synthesized in the U.A.M.S. Molecular Biology Core Facility. Restriction endonucleases, Vent polymerase, and T4 DNA ligase were from New England Biolabs.

EXAMPLE 2

Mutagenesis and Expression Vector Constructions

Starting with a previously prepared pET-9a (Novagen) HSV-1 thymidine kinase construct pET-TK1 (12), a 1.5 kb SalI-BamHI fragment was excised and subcloned into a pUC118 vector (pUC118-TK). Single-stranded pUC118-TK DNA was purified from cultures of JM107 after infection with helper phage M13K07 as previously described (18). Three mutagenic oligonucleotide primers were prepared to replace Gln-125 with either Asp-125, Asn-125 or Glu-125 as follows: ACAAGCGCCGACATAACAATG (SEQ ID No. 1) for Asp, ACAAGCGCCAACATAACAATG (SEQ ID No. 2) for Asn and ACAAGCGCCGAAATAACAATG (SEQ ID No. 3) for Glu. The three primers were used with an Amersham Sculptor in vitro mutagenesis kit as per manufacturers directions as adapted from Sayers, et al. (19). Plasmids isolated from the resulting colonies were sequenced by automated sequencing to confirm the presence of the mutation and its identity. After confirmation of each mutation, the DNA pieces were released by SalI-BamHI restriction digests and re-ligated back into the original pET-TK1 expression plasmid for transformation. The resulting colonies were again sequenced to confirm the presence of the mutated residues.

EXAMPLE 3

Enzyme Purification

E. coli BL21SY211 cells, in which T7 RNA polymerase is under control of the IPTG inducible lacUV5 promoter (20), were transformed with each pET-TK plasmid. These cells were grown to $A_{600}=0.6$, induced by 1 mM IPTG for 2.5 hours, and lysed in buffer A (20 mM Tris buffer, pH 8.1, 10% glycerol, 1 mM DTT, 40 mM KCl, 1 mM EDTA, 1 mM PMSF, and aprotinin (1 μg/ml)) by sonication for 3 minutes. The homogenate was then centrifuged at 10,000×g for 30 minutes to separate insoluble material. The soluble lysate was loaded onto a column of DE-52 in tandem sequence with a heparin agarose column (both 15×2 cm) and washed extensively with buffer A. The heparin agarose column was uncoupled from the DE-52 column and bound proteins were eluted in 50 ml buffer A plus 300 mM NaCl. The resulting fraction with thymidine kinase activity was concentrated to approximately 10 ml in an Amicon filtration apparatus, diluted with three volumes of buffer A (minus NaCl), and re-concentrated. This approach has reproducibly led to greater than 80% purified HSV-TK as determined by Coomassie blue staining with cumulative yields ranging from 0.5 to 2 mg total protein. The stability of the mutant enzyme preparations relative to wild-type preparations were identical when stored at −20° C. for up to 6 weeks (data not shown).

EXAMPLE 4

Enzyme Assays

The activity of the purified HSV-1 TK was determined using the following standard reaction mixture for thymidine as a substrate (12): 3 μg of protein, 4 μM [$^3$H-methyl] thymidine (0.1 mCi/mmol), 20 mM potassium phosphate, pH 7.6, 1 mM DTT, 5 mM ATP, 5 mM $MgCl_2$, 25 mM NaF, 40 mM KCl, and 0.5 mg/ml BSA in a total volume of 25 μl for 10 minutes at 37° C. To identify phosphorylated products, 20 μl of the reaction mixture was loaded onto a DE-81 filter and dried, washed once in 1 mM ammonium formate, twice more in 95% ethanol, and counted for radioactivity (12). Radioactivity was determined using an LKB 1214 Rackbeta liquid scintillation counter and corrected for background using controls with enzyme incubated in the absence of ATP. For TMPK activity, 20 μM [$^3$H-methyl]TMP was substituted for thymidine in the above assay mixture, and [$^3$H]TDP product was determined by separation from [$^3$H]TMP on thin layer PEI-cellulose plates developed in 0.35M LiCl (21). Amount of product converted to TDP was quantitated by scintillation counting of the excised TMP and TDP spots. The filter binding assay was used to quantitate the phosphorylation of [$^3$H]dC (200) μM and [$^3$H]AZT (200 μM) with the four enzymes. To compare relative enzymatic activities for [$^3$H]GCV (50 μM) and [$^3$H]ACV (50 μM), reactions were loaded onto small DE-52 columns packed in Pasteur pipettes as previously described (22). Unreacted nucleoside substrates do not bind to this resin, and phosphorylated products were eluted in 100 mM ammonium bicarbonate and quantified for radioactivity.

For determination of $K_m$ values of thymidine and GCV for the four enzymes, the filter binding assay was utilized. The basic reaction components were as above, and the following enzyme concentrations, substrate ranges and times were used under linear initial velocity conditions: for [$^3$H]thymidine: parent Gln-125TK: 0.1 μg TK, 0.1–4 μM, 10 min; Asn-125TK: 0.2 μg TK, 0.25–10 μM, 15 min; Asp-125TK: 4 μg TK, 0.1–2.5 μM, 30 min; Glu-125TK 0.5 μg TK, 0.5–2.5 μM, 15 min. For [$^3$H]GCV: parent Gln-125TK: 2 μg TK, 5–100 μM, 15 min; Asn-125TK: 0.6 μg TK, 0.5–15 μM, 15 min; Asp-125TK: Not determined; Glu-125TK 4 μg TK, 50–1000 μM, 25 min. Each reaction was done in triplicate. For calculation of kinetic constants, non-linear regression Michaelis-Menten analyses were done using PSI-PLOT version 5.0 (Poly Software International).

EXAMPLE 5

Photaffinity Labeling of HSV-1 TK

The TMP photoaffinity analog, [$^{32}$P]5-$N_3$dUMP, was synthesized enzymatically using HSV-1 TK, 5-azido-deoxyuridine and [g-$^{32}$P]ATP as previously described (10,12). For photolabeling studies, 10 μg of the DE-52/heparin agarose purified HSV-TKs were incubated with 10 mM [$^{32}$P]5-$N_3$dUMP for 10 seconds. The sample was then irradiated for 90 seconds with a hand-held UV lamp (254 nm UVP-11, Ultraviolet Products, Inc.) at a distance of 3 cm. Reactions were terminated by addition of an equal volume of 10% TCA, incubated on ice for 10 minutes, and pelleted by centrifugation at 13,000×g for 5 minutes. The protein was resuspended in a solubilization mixture (23) and separated on 10% SDS-polyacrylamide gels. Dried gels were exposed to film for 2 days.

EXAMPLE 6

Molecular Modeling of Substrate Interactions with HSV-1 TK

The active-site region of wild-type HSV-1 TK with bound thymidine or GCV was excised from the coordinates for the X-ray crystal structure of HSV-1 TK (kindly provided by Dr. Mark Sanderson (14)) and loaded into the Flexidock module of the molecular modeling program, SYBIL 6.3. Because the molecular interactions between bound thymidine and GCV were similar in the crystal structures except for rotation of Gln-125, this residue was defined as movable in the Flexidock program. As a control for this assumption, thymidine was placed in the Gln-125 HSV-1 TK active site and the lowest energy conformation determined. The lowest energy conformation was identical to that reported for thymidine in the crystal structure (14). Thus, lowest energy conformations for bound thymidine and GCV were done for the Gln-125, Glu-125, Asp-125 and Asn-125 active sites.

EXAMPLE 7

Expression and Characterization of HSV-1 TKs in Cell Lines

A Moloney murine leukemia virus derived plasmid for the expression of HSV-TK, termed pLENTK, has been previously constructed (24). A unique BspEI-MluI restriction fragment within the HSV-TK sequence of pLENTK contains the Gln-125 mutation site. This fragment was removed from wild-type plasmid and replaced with the analogous fragments encoding each mutant. The new pLEN-mutant-TK constructs were sequenced to confirm the presence of the mutation. Along with wild-type HSV-1 TK plasmid, each mutant-TK plasmid was transfected individually into the murine fibroblast cell line, NIH 3T3, and the human colon tumor cell line, HCT-116, using lipofectin reagent (GIBCO/BRL) (2 μg plasmid, 14 μl lipid per $1\times10^6$ cells). Cells were maintained in RPMI 1640 media and selected with G418 (200 μg/ml for 2 weeks) as previously described (24). At least eight individual G418 resistant cell clones were picked and grown up for further characterization. Each clone was screened initially for growth inhibition by 25 μM GCV. Those clones that were sensitive were further analyzed for HSV-TK protein expression by Western blot analysis with a polyclonal, rabbit anti-HSV-TK antibody (a gift from Dr. Margaret Black). For each clone, cell numbers were normalized to $1\times10^6$, and equal protein loading was confirmed for each sample by gel staining. Blotted HSV-1 TK protein bands were visualized on film using ECL chromophore reagents (Amersham). For analysis of GCV sensitivity of different clones, NIH3T3 and HCT-116 cell sets were seeded in 96 well plates in 0.1 ml media (15,000 cells/well). The next day, a dose range of GCV (0.005 to 5 mM, n=3) was added in 0.1 ml media. After 4 days, MTT (50 μg/well) was added for 1.5 hours, followed by DMSO solubilization of the cells and absorbance reading at 540 nm (25).

EXAMPLE 8

Metabolic Labeling with [$^3$H]Nucleosides

For metabolic labeling, cells ($1-2\times10^6$) were labeled in triplicate with 2 μCi [$^3$H]GCV (8 mM) for 18 hours, then nucleotides were extracted from pelleted cells in 0.2 ml 70% methanol at 4° C. for 15 minutes as previously described (21, 24). An aliquot of each methanol soluble supernatant was analyzed for radioactivity b y scintillation counting. The methanol insoluble pellets, representative of a crude DNA fraction, were resuspended in 0.15 ml water and also counted for radioactivity. For deoxypyrimidines, cells were grown to confluency in 60 cm² plates, and either 2 μCi [$^3$H]thymidine (2 μM final) or 2 μCi [$^3$H]dC (10 μM final) were added for 1 or 2 hours respectively prior to extraction in 70% methanol. Methanol-soluble extracts were concentrated by evaporation under nitrogen, and separated on PEI-cellulose thin layer chromatography plates developed in 0.8 M LiCl for GCV or 0.35 M LiCl for thymidine/dC as previously described (21).

EXAMPLE 9

GCV Sensitivity and Bystander Effect Clonal Dilution Assays

For determination of GCV sensitivity, parental HCT-116 and each HSV-1 TK expressing cells were seeded in 24 well plates ($2\times10^5$/well) in 1 ml of media. The next day, 0, 0.1, 1 or 10 μM GCV was added to each cell line in triplicate. After 24 hours, for each well the media was removed, cells were rinsed twice in fresh media, trypsinized, then media was added to 1 ml per well. Each well of cells was then sequentially diluted from 1:10 to 1:10,000 in 1 ml of fresh media on a separate 24 well plate. After 7 days, surviving cell colonies were fixed in 100% methanol, stained with 0.1% methylene blue and counted. For bystander effect assays, each of the three HSV-1 TK expressing cell lines were plated with parental HCT-116 cells (total $2\times10^5$/well) in the following proportions: (parental: HSV-1TK cells) 100%:0; 95%:5%; 90%:10%; 75%:25%; 50%:50% and 0:100%. After two days, 25 μM GCV was added in 1 ml fresh media. After 24 hrs, the media was removed and cells from each well were diluted from 1:10 to 1:10,000 as described above. After 7 days, surviving cell colonies were fixed and stained for counting.

EXAMPLE 10

DAPI-Staining of Apoptotic Cells

Parental HCT-116 cells and each HSV-1 TK expressing cell line were plated ($5\times10^4$ cells/well) in 8-well plastic chamber slides (Lab-Tek) and treated plus or minus 25 μM GCV for 36 or 84 hrs. A t either time point, cells were washed with phosphate-buffered saline followed by staining in 1 μg/ml DAPI (4',6'-diamidine-2'-phenylindoledihydrochloride) in 100% methanol at 37° C. for 10 min. After rinsing, the stained cells were visualized with a Zeiss flourescent microscope at 40× magnification with a DAPI-specific filter.

EXAMPLE 11

Caspase 3 Assay

Caspase 3-like activity was determined in parental HCT-116 and each HSV-1 TK expressing cell line treated for 50 hrs plus or minus 25 μM GCV using an Apo-Alert CPP32/Caspase 3 Colorimetric Assay kit with the peptide substrate, DEVD-pNA, as per manufacturers instructions (Clontech Laboratories, INC.). GCV-treated and untreated cells were grown in 25 cm² flasks, and cell numbers were determined using a hemocytometer prior to analysis. Assays were done in triplicate with protein extracts derived from $2\times 10^6$ cells. The amount of Caspase 3-like activities were quantitated using a Shimadzu UV/VIS spectophotometer set at 405 nm.

EXAMPLE 12

Cell Cycle Analysis

Parental HCT-116 cells and each HSV-1 TK expressing cell line were grown to 60% confluency in 25 cm² flasks and treated for 24 hours plus or minus 25 μM GCV. Following drug incubation, cells were removed by trypsin and total cell numbers determined. Following two phosphate buffered saline rinsing and centrifugation cycles, the cell pellets were resuspended in 1 ml of 70% ethanol and stored at 4° C. until further analysis. Just prior to cell cycle analysis, the ethanol was removed and cell pellets were resuspended in phosphate-buffered saline plus RNAase (0.1%) and propidium iodide (1 mg/ml) for 30 minutes on ice. Flow cytometry measuring propidium iodide fluorescence was done with a Becton-Dickinson FACScalibur instrument. Cell cycle distribution of the cells were detemined using MODFIT computer software

EXAMPLE 13

Mutagenesis and Expression of Gln-125 Mutants of HSV-1 TK

Expression plasmids derived from wild-type pET-TK1 (12) encoding the Asp, Asn or Gln changes were individually transformed into BL21 *E. coli,* grown and induced with IPTG. After cell pelleting and sonication, the resulting mutant HSV-TKs, along with wild-type HSV-TK and pET9a control preparations, were partially purified over tandem DE-52 and heparin agarose columns. This is a modification of the previously described purification method for HSV-1 TK (12), in that the pH of the lysis buffer has been changed from pH 7.6 to pH 8.1. This change allows the bulk of expressed HSV-1 TK to flow-through the DE-52 column, instead of weakly absorbing as in the previous procedure (12). Under conditions utilized, no TK or TMPK activities in the *E. coli* pET-9a extracts were detected (data not shown).

EXAMPLE 14

Enzymatic Activities of the Gln-125 HSV-1 TK Mutants

As an initial screen for activity, each expressed HSV-1 TK enzyme was assayed for phosphorylation of the following substrates: thymidine (4 µM), TMP (20 µM), ACV (50 µM), GCV (50 µM), deoxycytidine (dC, 200 µM), or 3'-azido-2', 3'dideoxythymidine (AZT, 200 µM). Enzymatic conditions for optimal wild-type HSV-1 TK activities were utilized, thus results presented in Table 1 for each substrate were normalized to 100% values for comparative purposes. As expected, the wild-type Gln-125 HSV-1 TK efficiently phosphorylated each of these substrates. For each mutant, there was a striking decrease in their ability to phosphorylate pyrimidine nucleosides, and minimal TMPK activity for the TMP substrate. For metabolism of GCV and ACV, the Asn-125TK retained most of these phosphorylation activities, while activities for the Asp-125TK and Glu-125TK were decreased to 14% and 7% for ACV and 0.7% and 5% for GCV respectively.

TABLE 1

Analysis of Reaction Products for Wild-type and Mutant HSV-1 TKs
PRODUCT FORMATION
(% of wild-type Gln-125)

| TK Enzyme | TMP | TDP | GCVMP | ACVMP | dCMP | AZTMP |
|---|---|---|---|---|---|---|
| Gln-125 (WT) | 100 | 100 | 100 | 100 | 100 | 100 |
| Glu-125 | 43 | 7 | 5 | 7 | 0.2 | 48 |
| Asn-125 | 22 | 6 | 85 | 92 | 0.2 | 9 |
| Asp-125 | 0.5 | 4 | 0.7 | 14 | >0.1 | 8 |

Due to these observed differences in purine versus pyrimidine metabolism, and because of the use of HSV-1 TK in cancer gene therapy applications with GCV (3,4), the $K_m$ and $k_{cat(app)}$ for thymidine and GCV were determined for each of the four HSV-1 TKs and listed in Table 2. Unlike the substrate screening assays presented in Table 1, linear velocity conditions for each enzyme and substrate were established prior to $K_m$ determinations. For thymidine, the $K_m$s increased relative to wild-type enzyme approximately 3-fold for the Glu-125 enzyme, 20-fold for the Asn-125 enzyme and 6000-fold for the Asp-125 enzyme. The $k_{cat}$ doubled for the Asp-125 and Asn-125 enzymes, while a 20-fold decrease in $k_{cat}$ was determined for the Glu-125TK. For GCV, the $K_m$ decreased from 69 µM for wild-type enzyme to 50 µM for the Asn-125TK, while the $K_m$ increased to 473 µM for the Glu-125 enzyme. These mutations also caused a 6-fold and 12-fold decrease respectively in the $k_{cat}$ compared to wild-type enzyme. Interestingly, no linear velocity conditions could be established for the Asp-125TK with GCV. As was shown in Table 1, this enzyme will phosphorylate a small amount of GCV, however, it does not generate product in an initial velocity-dependent manner. The basis for this lack of activity was not further evaluated.

TABLE 2

Kinetic Constants of HSV-1 TK Gln-125 Mutants for Thymidine and Ganciclovir

| | THYMIDINE | | | GANCICLOVIR | | |
|---|---|---|---|---|---|---|
| HSV-1TK | $K_m$(µM) | $k_{cat}$(s$^{-1}$) | $k_{cat}/K_m$ (M$^{-1}$s$^{-1}$) | $K_m$(µM) | $k_{cat}$(s$^{-1}$) | $k_{cat}/K_m$ (M$^{-1}$s$^{-1}$) |
| Gln-125 WT | 0.9 | 0.06 | $6.7 \times 10^4$ | 69 | 0.47 | $6.8 \times 10^3$ |
| Asn-125 | 20 | 0.13 | $6.5 \times 10^4$ | 50 | 0.08 | $1.7 \times 10^3$ |
| Glu-125 | 3 | 0.003 | 844 | 473 | 0.04 | 82 |
| Asp-125 | 6000 | 0.11 | 18 | N.D. | N.D. | N.D. |

N.D. - not determined

EXAMPLE 15

Photoaffinity Labeling of the Gln-125 HSV-1 TK Mutants

The thymidine and TMP photoaffinity analog, [$^{32}$P]5-azido-dUMP, has proven useful as an active-site cross-linking reagent for studying HSV-1 TK (10, 12). This analog was used for photocrosslinking of the four HSV-1 TKs. As shown in FIG. 1, [$^{32}$P]5-azido-dUMP was photoincorporated efficiently into the wild-type Gln-125 enzyme, but only trace photoincorporation was detected for the three mutant HSV-1 TKs. These results further demonstrate the weak binding affinities of the three mutant HSV-1 TKs for pyrimidine substrates.

EXAMPLE 16

Molecular Modeling Comparisons of Thymidine and Ganciclovir in the Gln-125 and Mutant HSV-1 TK Active Sites The Flexidock component of the molecular modeling program, SYBIL 6.3, was used with the coordinates of the wild-type Gln-125 HSV-1 TK crystal structure (14) to dock thymidine or GCV in the active site of each of the four HSV-1 TK enzymes. As shown in FIG. 2, loss of hydrogen bonding between the N3 and O4 of the thymine base and Asn-125 or Asp-125 may be the molecular basis for the decreased pyrimidine substrate phosphorylation activities of these enzymes. This analysis predicts that the Glu-125 enzyme may still form one hydrogen bond, thus retaining its thymidine phosphorylation activity. Analysis of GCV in the active site predicts that it is still able to maintain hydrogen bonding with the Asp, Asn, or Glu residues (data not shown), and thus could contribute to the retention of this phosphorylation activity with the Asn-125 mutant. Introduction of the negatively charged Asp and Glu residues clearly attenuated the GCV phosphorylation activities relative to the Asn mutation, and it is thus likely that this charge difference also contributes to the observed changes in enzymatic properties.

EXAMPLE 17

Figure 3A:
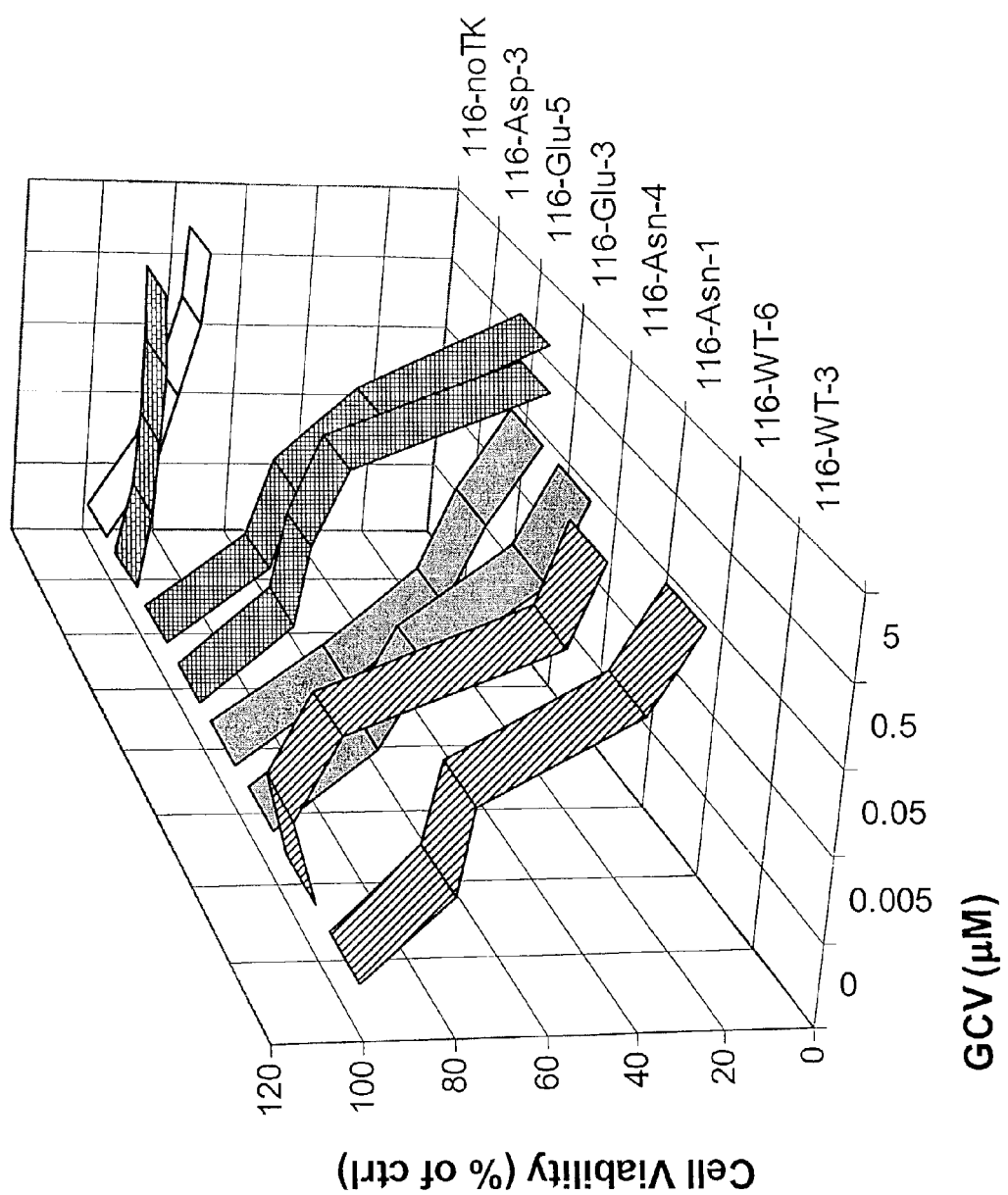
FIG. 3A: NIH3T3 cell lines.
Figure 3B:
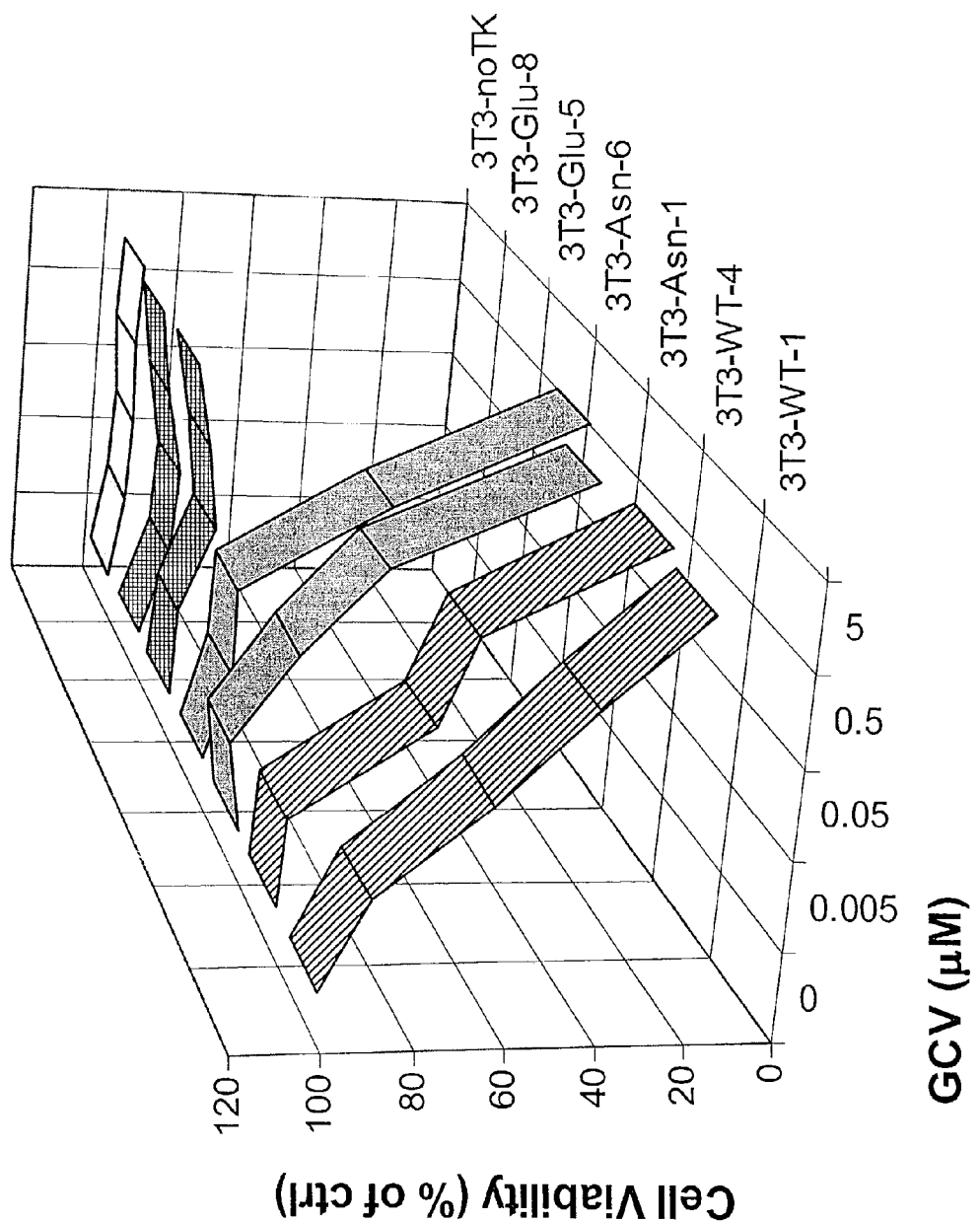
FIG. 3B: HCT-116 cell lines; parental cells (noTK, dark bands); Asp125TK (Asp-#, brick band); Glu-125TK (Glu-#, cross-hatch bands); Asn-125TK (Asn-#, gray bands); wild-type HSV-1 TK (WT-#, striped bands).

Cellular Expression of HSV-1 TK and Sensitivity to GCV Killing cDNA for each mutant was incorporated into a Moloney murine leukemia virus plasmid (24). The plasmids for wild-type HSV-1 TK and each mutant were individually transfected into either NIH3T3 cells or the human colon tumor cell line, HCT-116. Following drug selection in G418, individual cell clones were evaluated for sensitivity to GCV and relative levels of HSV-1 TK expression. Using an HSV-1 TK antibody and extracts normalized by protein and cell number, the relative expression levels of HSV-1 TK in each cell clone were determined. Cell sets having equivalent expression of an HSV-1 TK and roughly equivalent cell growth rates were identified and selected for comparative study. As shown in FIG. 3, these NIH3T3 and HCT-116 cell sets were plated in 96 well plates and evaluated for dose dependent cell killing by GCV for 4 days. Increasing GCV concentrations led to proportionally more cell killing in the wild-type or Asn-125TK clones tested, and apparently both enzymes function similarly in regards to intracellular GCV metabolism and effects on cell viabilities. For the Glu-125TK mutants, minimal cell killing was observed in the NIH3T3 cells. However, the Glu-125TK expressed in the HCT-116 cells led to minor decreases in cell viability at lower GCV concentrations, but at the highest concentration, 5 μM, cell viabilities dropped precipitously. For the Asp-125TK expressing HCT-116 cell lines, GCV had little effect on cell viability, although expression of HSV-1 TK protein was detected by antibody (data not shown). As expected, GCV had little effect on the cell viabilities of the non-HSV-1 TK expressing parental cells.

expression based on Western blot determinations. In this study, these two sets of HSV-1 TK-expressing NIH 3T3 and HCT-116 cell lines were evaluated for intracellular metabolism of [$^3$H]GCV, [$^3$H]thymidine, or [$^3$H]dC. Cells were labeled with [$^3$H]GCV for 18 hours, then nucleotides were extracted in ice-cold 70% methanol as previously described (21, 24). The data in Table 3 summarize the amount of total nucleotide metabolites isolated in the methanol-soluble extracts (pmol/$10^6$ cells) as well as the total amount of methanol-insoluble metabolites representative of incorporation into DNA. The Asn-125TK metabolizes GCV at (or near) equal levels to the wild-type HSV-TK in both cell lines. The methanol-insoluble data, while only a crude indicator of [$^3$H]GCV incorporation into DNA, reflects the numbers obtained with the soluble extracts. As compared with the non-HSV-TK-expressing HCT-116 cells and consistent with data in the previous study (24), minimal [$^3$H] GCV metabolism was detected in the Asp-125TK cells and these cells were not further evaluated.

TABLE 3

Total Methanol Soluble and Insoluble [$^3$H]-Metabolites (pmol/$10^6$ cells)

| NIH3T3 Cell line | NIH3T3 [$^3$H]GCV[a,b] | NTH3T3 [$^3$H]GvDNA[c] | HCT116 [$^3$H]GCV[b] | HCT116 [$^3$H]GvDNA[c] | HCT116 [$^3$H]T[b] | HCT116 [$^3$H]dC[b] |
|---|---|---|---|---|---|---|
| parent | 2.8 | 2.8 | 1.1 | 1.2 | 2.4 | 1.1 |
| Gln-125TK | 498 | 48 | 1216 | 141 | 52.0 | 4.5 |
| Asn-125TK | 585 | 42 | 1085 | 133 | 8.0 | 1.2 |
| Glu-125TK | 3.6 | 2.6 | 33 | 27 | 3.3 | 0.9 |
| Asp-125TK | N.D. | N.D. | 1.0 | 1.6 | N.D. | N.D. |

[a]Each value is the mean of three independent data points;
N.D. = not determined
[b]Methanol-soluble nucleotide metabolites
[c]Methanol-insoluble metabolites

EXAMPLE 18

Metabolic Labeling with [$^3$H]GCV [$^3$H]thymidine, and [$^3$H]dC

NIH3T3 fibroblasts and the human tumor cell line HCT-116 were transfected with wild-type HSV-1TK or with one of three site specific mutants of amino acid Gln-125. From a panel of multiple HSV-1TK expressing clones, a subset of clones from each cell line expressing wild-type HSV-1 TK, the Asn-125 HSV-1 TK mutant (Asn-125TK) and the Glu-125 HSV-1 TK mutant (Glu-125TK) were selected for comparatively equivalent levels of HSV-1 TK protein The methanol-soluble metabolites were further separated into their constituent phosphorylated GCV metabolites by thin layer chromatography (21). As presented in Table 4, the predominant metabolite in each HSV-TK-expressing cell line was GCVTP. In both HCT-116 and NIH3T3 cell lines, the Asn-125TK cells indicated slightly higher levels of GCVTP as compared to wild-type HSV-1 TK cell lines. The Glu125-TK in HCT-116 cells resulted in a 23-fold or greater decrease in GCVTP levels, while levels of GCVTP in the NIH3T3 cells was only weakly detected. This difference in the levels of GCVTP in the two Glu-125TK expressing cell lines could explain the lack of sensitivity to GCV killing observed for the NIH3T3 Glu-125TK cell lines.

TABLE 4

Phosphorylated Metabolites of GCV and Thymidine from HCT-116 and NIH3T3 Cell Clones.
PHOSPHORYLATED METABOLITES (pmol/$10^6$ cells)

| | 3T3 GCVMP | 3T3 GCVDP | 3T3 GCVTP | 116 GCVMP | 116 GCVDP | 116 GCVTP | 116 TMP | 116 TTP |
|---|---|---|---|---|---|---|---|---|
| parent | 0.2 | 0 | 0 | 0.4 | 0 | 0.4 | 0.1 | 0.2 |
| Gln-125TK WT | 12 | 22 | 232 | 96 | 101 | 415 | 1.2 | 9.5 |
| Asn-125TK | 11 | 21 | 272 | 95 | 104 | 533 | 0.2 | 09 |
| Glu-125TK | 0 | 0 | 1.6 | 3.0 | 2.5 | 18 | 0.2 | 0.4 |

Because the enzymatic data indicated that the Asn-125 and Glu-125 mutations had altered deoxypyrimidine substrate utilization, the metabolism of thymidine and dC in the HCT-116 cell set were examined. Cells were grown to confluency and labeled with either [$^3$H]thymidine or [$^3$H]dC for 1 or 2 hours respectively prior to methanol extraction. If labeling was done in sub-confluent, dividing cultures, it was found that the metabolite numbers reflected cell growth rates, and therefore cellular kinase activities rather than that of HSV-TK activity (data not shown). As presented in the last two columns of Table 3, the levels of deoxypyrimidine metabolites extracted from the mutant HSV-TK cells were analogous to those isolated from parental HCT-116 cells rather than the wild-type HSV-TK cells. As shown in Table 4, the levels of TMP and TTP separated from the methanol-soluble fractions of the [$^3$H]thymidine labeled HCT-116 Asn-125 TK and Glu-125TK cells were similar to parental HCT116 cells rather than the wild-type HSV-1 TK expressing 116 cell line. These metabolite levels support the enzymatic data a n d highlight the altered substrate specificities of the Glu-125 and Asn-125 HSV-1 TKs. When expressed in cell lines, these mutant forms of HSV-1 TK appear to function more as GCV kinases rather than thymidine kinases.

EXAMPLE 19

Comparative GCV Sensitivities and Bystander Effect

Figure 4:
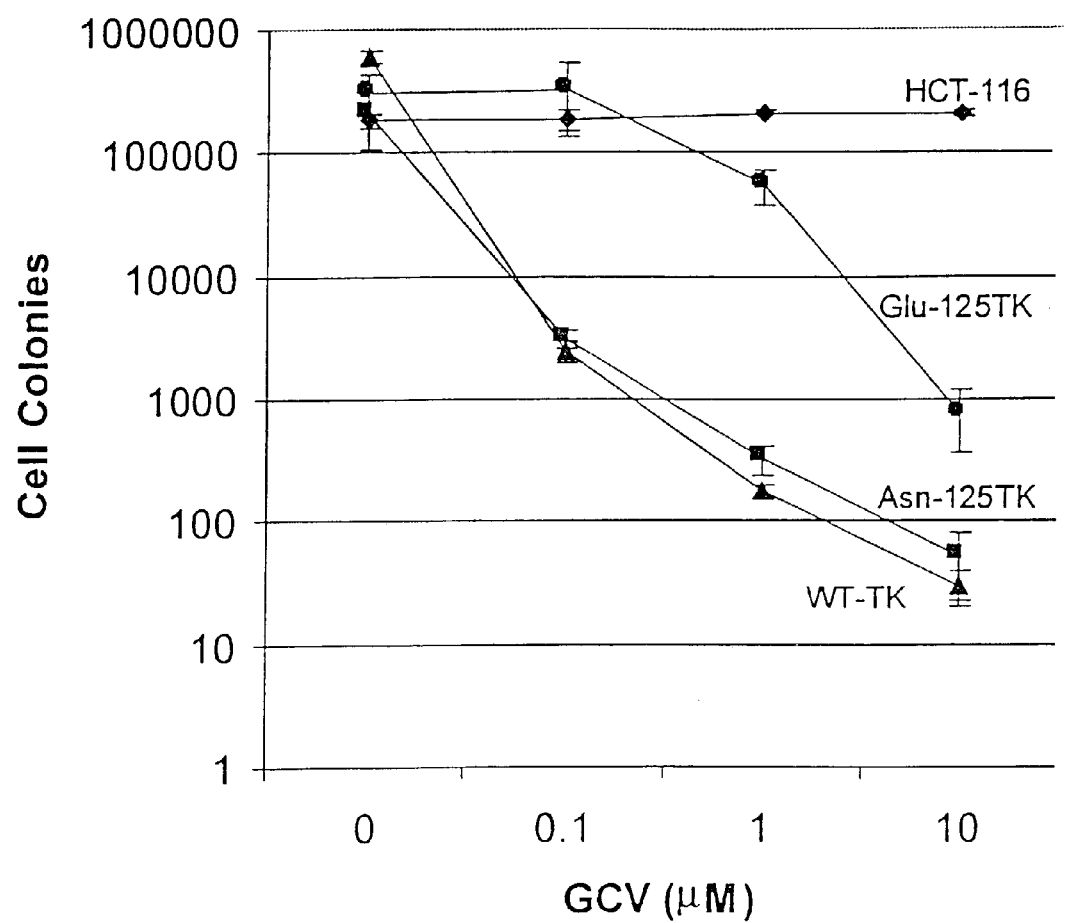
FIG. 4 shows clonal dilution assays for GCV sensitivity. Parental HCT-116 (large square), wild-type HSV-1 TK cells (triangle), Asn-125TK cells (small square) and Glu-125TK cells (diamond) were treated with 0, 0.1, 1 or 10 µM GCV in triplicate for 24 hours. After this time, each well of cells was sequentially diluted from 1:10 to 1:10,000 in 1 ml of fresh media on a separate 24 well plate. After 7 days, surviving cell colonies were fixed in 100% methanol, stained with 0.1% methylene blue and counted.

Studies using an MTT cell viability assay determined that HCT-116 cells expressing the poor GCV metabolizing Glu-125 HSV-1 TK were just as sensitive to GCV killing as the high-GCV metabolizing wild-type or Asn-125TK enzyme. Another striking aspect of this cell killing was the large number of apparently cytostatic, non-viable GCV-treated Glu-125TK-expresssing cells that remained on the plate and did not stain with MTT. Because the Glu-125TK expressed in NIH3T3 cells had little effect on their GCV sensitivities, only the HCT-116 cell panel was evaluated in the rest of the study. Using the same panel of HSV-TK-expressing HCT-116 cell lines normalized to one another and characterized for equivalent expression of HSV-1 TK protein, more sensitive clonal dilution assays were done. Cells previously plated in 24 well plates were treated with GCV (0–10 µM) in triplicate for 24 hours. Following drug removal, cells were diluted and replated in fresh media from dilutions of 1:10 to 1:10,000. Surviving cell colonies were counted 6–7 days later. As shown in FIG. 4, 0.1 µM GCV treatment led to a 2-log decrease in the wild-type and Asn-125TK expressing cell colony numbers. In the same cell lines treated with 10 µM GCV, a 4-log decrease in colony numbers were determined. In contrast, the Glu-125TK-expressing cells treated with 0.1 GCV µM caused no reduction in cell colony numbers, while 1 µM or 10 µM GCV led to 0.7-log and 2.5-log decreases in colony numbers respectively. At higher concentrations of GCV (20–110 µM), the expressed Glu-125TK led to over 3-log reductions in colony numbers (data not shown).

Figure 5:
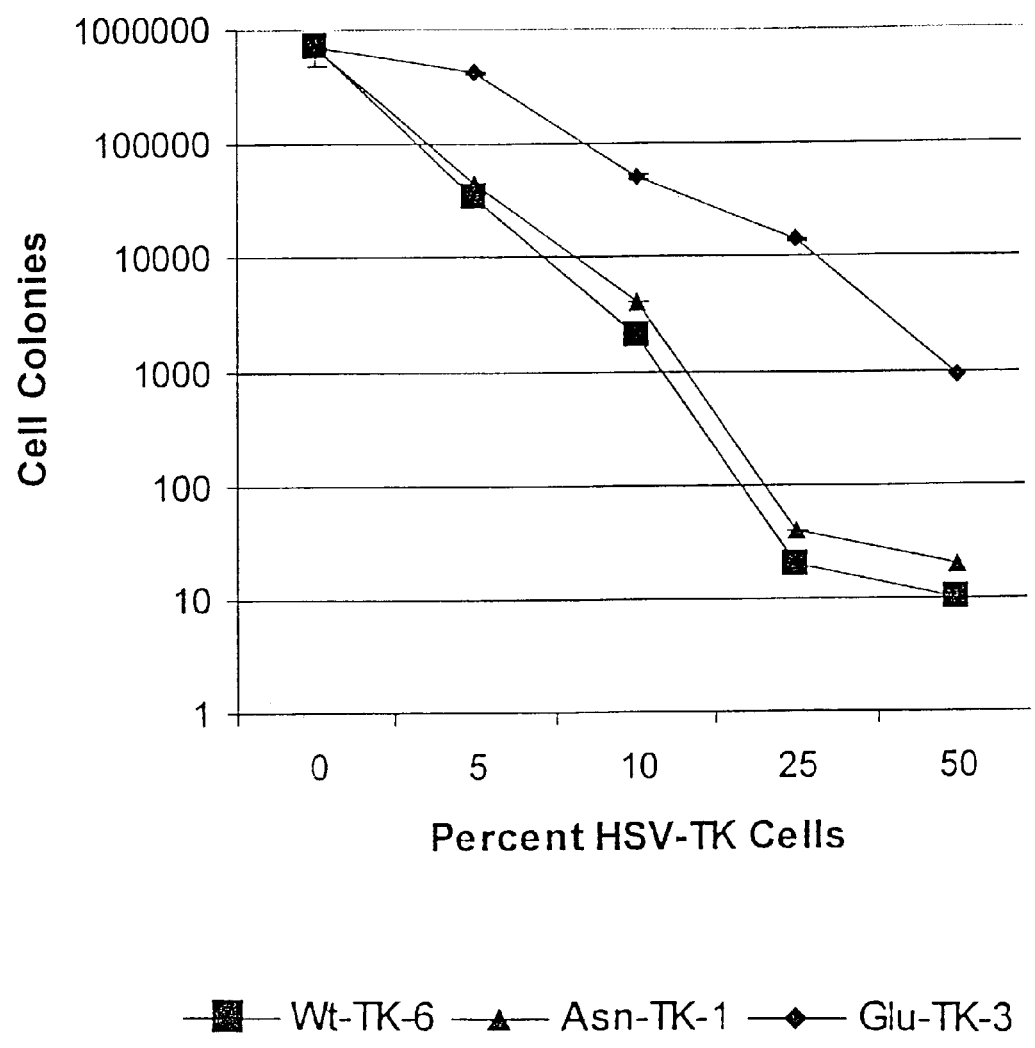
FIG. 5 shows clonal dilution assays for bystander effect cell killing. Each of the three HSV-1 TK expressing cell lines were plated with parental HCT-116 cells (total 2×10$^5$/well) in the following proportions: (parental: HSV-1TK cells) 100%:0; 95%:5%; 90%:10%; 75%:25%; 50%:50% and 0:100%. Cells were treated with 25 mM GCV for 24 hours, then each well of cells was sequentially diluted from 1:10 to 1:10,000 in 1 ml of fresh media on a separate 24 well plate. After 7 days, surviving cell colonies were fixed in 100% methanol, stained with 0.1% methylene blue and counted.

It has been previously established that HCT-116 cells expressing HSV-1 TK are sensitive to bystander effect cell death via a connexin-43 gap junction mediated transfer of GCV metabolites (24). To evaluate this effect in the HSV-1 TK 116 cell panel, clonal dilution assays were performed with different proportions of HSV-1 TK expressing cells (5–50%) mixed with HCT-116 parental cells. Cell populations were treated with 25 µM GCV for 24 hours, and then diluted from 1:10 to 1:10,000. As shown in FIG. 5, only 5% wild-type or Asn-125TK-expressing cells were required to cause a greater than 1-log decrease in cell colony numbers. In these same cell lines, a greater than 4-log reduction in cell colony numbers was detected with 25% and 50% proportions of HSV-1 TK-expressing cells. For the Glu-125TK-expressing cells, a 1-log GCV-mediated bystander effect was observed at 10% proportions, and a near 3-log decrease was detected with the 50% proportions. Even though the bystander effect with the Glu-125TK-expressing cells was clearly attenuated relative to the other two cell lines, the Glu-125 mutant was still able to generate significant bystander effect cell killing.

EXAMPLE 20

Cell Cycle Analysis

GCV has also been previously reported to induce S and G$_2$-M phase cell cycle arrest in HSV-1 TK expressing glioma and melanoma cell lines (36–38). Therefore, the effect of 24 hr GCV treatment on the cell cycling of parental and the three HSV-1 TK-expressing cell lines was examined by flow cytometry of propidium iodide stained cells. As shown in FIGS. 6A and 6B and Table 5, GCV treatment of HCT-116 parental, non-HSV-1 TK-expressing cells had little effect on the percentage of cells in each phase of the cell cycle as compared with untreated cells. In the wild-type and Asn-125TK-expressing cell lines, GCV treatment (FIGS. 6D and 6F) led to an increase in the proportion of cells in the S-phase, and undetectable percentages in G$_2$-M phase when compared to untreated cultures (FIGS. 6C and 6E). For the Glu-125TK-expressing cells, over 60% of the GCV treated cells were in S-phase and undetectable percentages were in G$_2$-M (FIG. 6H). These results may reflect the more cytostatic effects of GCV observed with the Glu-125TK-expressing cells.

TABLE 5

Cell Cycle Profiles of GCV Treated Cell Lines

| Cell Line | Cell Cycle Phase (%) | | |
|---|---|---|---|
| | G$_0$/G$_1$ | S | G$_2$/M |
| HCT-116 (−GCV) | 43.3 | 35.0 | 21.7 |
| HCT-116 (+GCV) | 39.0 | 44.0 | 17.1 |
| WTGln-125TK (−GCV) | 65.8 | 18.4 | 15.8 |
| WTGln-125TK (+GCV) | 60.1 | 39.9 | 0 |
| Asn-125TK (−GCV) | 63.4 | 18.0 | 18.6 |
| Asn-125TK (+GCV) | 70.0 | 30.0 | 0 |
| Glu-125TK (−GCV) | 62.4 | 8.5 | 29.1 |
| Glu-125TK (+GCV) | 39.0 | 61.0 | 0 |

EXAMPLE 21

DAPI-Staining and Caspase 3 Apoptosis Assays

The differential dose responses, morphological features and cell cycle patterns associated with the Glu-125 HSV-1 TK-expressing cells treated with GCV suggested induction of a distinct cell death mechanism different from that observed in wild-type HSV-1 TK-expressing cells. It has been previously established that GCV treatment of wild-type HSV-1 TK-expressing cell lines results in induction of apoptosis (36–37, 39–40). Therefore, two late-stage apoptosis assays, nuclear DAPI-staining and caspase-3 activation, were done for GCV treatments of the three HSV-1 TK-expressing HCT-116 cell lines. As shown in FIG. 7, DAPI-stained nuclei of wild-type and Asn-125TK-expressing cells treated with GCV for 36 or 84 hrs indicated progressive increases in condensed and fragmented nuclei characteristic of apoptosis. Also, the DAPI-staining of these cell lines indicates a GCV-specific nuclear swelling of pre-apoptotic cells and enhanced staining of nucleoli. This nuclear swelling in response to GCV has been observed within 12 hours of GCV administration in wild-type HSV-1TK HCT-116 cells (data not shown). For the Glu-125 HSV-1TK expressing cells, 36 hrs of GCV treatment led to fewer swelled nuclei and little evidence of apoptotic nuclei, although distinct staining of condensed nucleoli was observed. Even after 84 hrs of GCV treatment of these cells, there were still comparatively fewer changes in nuclear morphologies of the Glu-125TK cells compared to the wild-type or Asn-125 HSV-1TK expressing cells. There was apparent nuclear swelling in the Glu-125TK cells, and this reflects the morphological appearance of the cells observed in the MTT assays. Under identical treatment conditions, GCV treatments of parental, non-HSV-1TK expressing HCT-116 cells indicated none of the nuclear swelling or apoptotic fragmentations seen in the three HSV-1 TK-expressing cell lines (data not shown).

Figure 8:
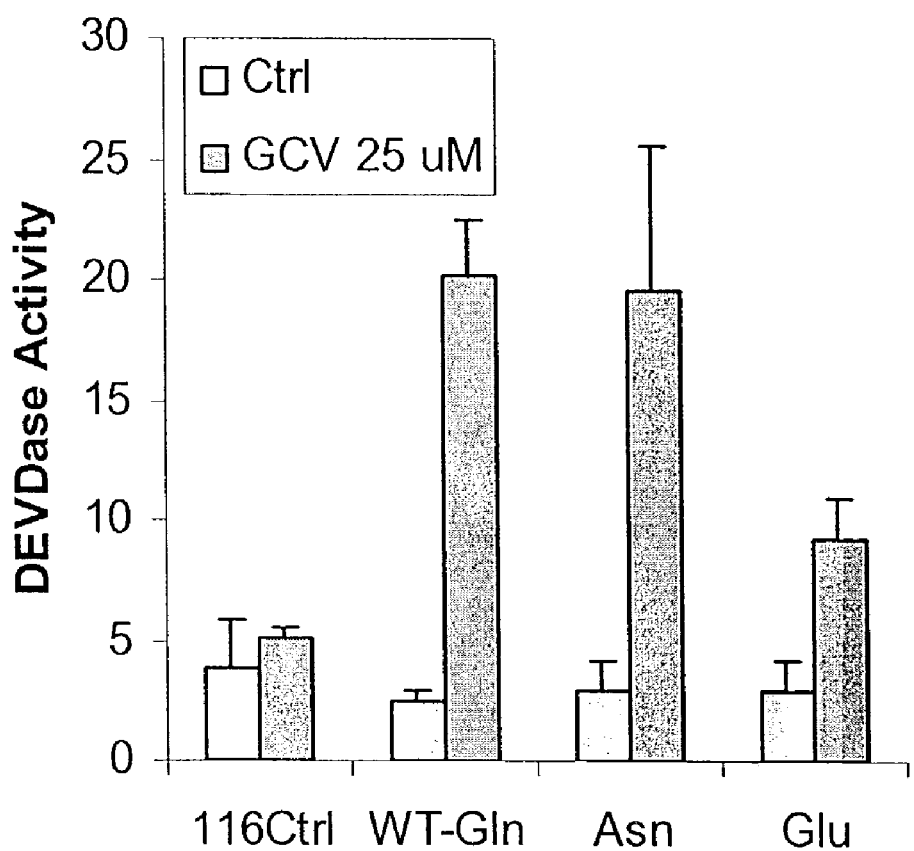
FIG. 8 shows activation of Caspase 3 in response to GCV treatment. Parental HCT-116, wild-type HSV-1TK, Asn-125TK and Glu-125TK-expressing HCT-116 cells were treated with 0 (black bars) or 25 µM GCV (gray bars) for 4 days. Cell lysates were prepared and caspase 3 assays performed using a colorimetric ApoAlert CPP32/Caspase-3 kit as per manufacturers instructions (Clontech). Relative caspase 3 activity was determined by O.D. 405 nm readings of the cleaved DEVD-pNA substrate and presented as DVE-Dase activity.

A more direct analysis of apoptotic activity was done by assaying the activation of the executioner protease, caspase 3. Activation of the zymogen form of caspase 3 has been implicated as component of the latter execution phase of apoptosis, and the substrate proteins cleaved by activated caspase 3 and related enzymes are responsible for the end-stage morphological and intracellular changes associated with apoptotic cell death (41–42). Caspase 3 activity was determined in different cell extracts derived from GCV-treated and control cells using a colorimetric assay with the peptide substrate DVED (SEQ ID No. 4). As shown in FIG. 8, the DVED-ase activity of GCV-treated Glu-125 HSV-1TK cells was three times lower than that observed for GCV-treated wild-type or Asn-125 HSV-1TK-expressing cells. Co-incubation of GCV-treated wild-type HSV-1 TK-expressing cells with the competing peptide DVED (SEQ ID No. 4) resulted in caspase 3 activities near untreated control cell values (data not shown). Thus, the results of the DAPI-staining and caspase 3 assays are consistent with an altered apoptotic response and cell death pathway in GCV-treated Glu-125 HSV-1TK-expressing cells. The cumulative results of this study are consistent with two distinct cell death pathways induced by GCV treatment in the same HCT-116 cell line background that is dependent on the distinct enzymatic properties of HSV-1 TK.

Discussion

Multiple X-ray crystal structures of HSV-1 TK have highlighted the importance of Gln-125 in forming hydrogen bonds with pyrimidine and purine substrates like GCV (13–17). It was demonstrated that fairly conservative mutations of Gln-125 to Glu, Asp or Asn can have profound effects on substrate specficity and overall enzyme activity. Cumulatively, the data indicate that all three mutations appear deficient in binding of TMP, which is the second substrate for the TMP kinase activity of wild-type HSV-TK. The inability of each mutant enzyme to photoincorporate the active-site directed photoaffinity analog, [$^{32}$P]5-azido-dUMP, further demonstrates this lack of TMP binding. It was previously determined that 5-azido-dUMP covalently crosslinks to an amino acid in the peptide comprising residues 112–132 (10). The lack of photolabeling of the mutant enzymes suggest that the site of crosslinking is at or near the vicinity of Gln-125. The Asn-125 mutant utilizes thymidine as a substrate poorly, but retains ganciclovir and acyclovir phosphorylation activities. Molecular modeling of the three mutations using a Flexidock program has predicted that loss of hydrogen bonding between thymidine and the Asp-125 or Asn-125 mutants contributes to the altered activities, while hydrogen bonding with each mutant and GCV is still retained. Clearly, the introduction of a negative charge (Glu, Asp) in the active site versus the more conserved Asn residue is another contributing factor to the altered activities. When expressed in HCT-116 cell lines, the Asn-125 and Gln-125 HSV-1 TKs are as effective as wild-type HSV-1 TK at inducing GCV mediated cell killing.

A previous study evaluated the effect that single amino acid substitutions at Gln-125 (Asn, Asp, Glu, or Leu) had on thymidine and ACV phosphorylation (17). In this study, it was reported that their Glu-125 mutant had no detectable activities, and the Asn-125 mutant had a 50-fold and 3-fold increase in the $K_m$s of thymidine and ACV respectively (17). These mutant HSV-1 TKs were not expressed in mammalian cell lines. These results differ significantly from the data presented herein for the HSV-1 TK mutants. Other than the expression of their HSV-1 TK mutant enzymes as glutathione-S-transferase fusion constructs (17), the reasons for the discrepancies in the results for the same mutants is not clear. In other previous reports, a series of random insertional oligonucleotide mutagenesis studies on HSV-1 TK have demonstrated the catalytic role of the amino acids spanning residues 159–172 (27–29), and many mutants have been identified which have altered or improved substrate specificities for GCV and ACV (28, 29). As a goal toward improving HSV-1 TK gene therapy strategies, some of the mutant HSV-1 TKs generated by random insertional mutagenesis were tested for cell killing efficacy in mammalian cells (29). One of these mutants, which had four changed residues (Ile-160 to Leu; Phe-161 to Leu; Ala-168 to Val; Leu-169 to Met), was shown to have 43-fold and 20-fold greater sensitivities to cell killing with GCV and ACV respectively (29). The $K_m$ of GCV for this mutant was 5-fold lower than wild-type HSV-1 TK, and the $k_{cat}$ of the mutant enzyme for thymidine, ACV and GCV remained the same as wild-type HSV-1 TK (29). Because these amino acid changes occur in a distinct catalytic region of HSV-1 TK and the Gln-125 appears to be only involved in nucleoside base binding (13–17), it should be possible to construct hybrid HSV-1 TKs comprising mutations from both sites to generate an enzyme with minimal TK/TMPK activities and maximal acyclic purine nucleoside phosphorylation activities.

In other cell culture studies, it has been demonstrated that the more HSV-1 TK protein expressed in a cell, the more efficient GCV metabolism and cell killing are (30–33). Whether by improving expression or catalytic efficiencies, these cumulative results for HSV-1 TK indicate that any method of increasing GCV metabolism could result in increased therapeutic benefits. Because the $K_m$ for thymidine is over 70–100 times lower than that of GCV for wild-type HSV-TK (29), it was hypothesized that in a cellular environment the Asn-125 mutant would act primarily as a GCV kinase, particularly as thymidine and its metabolites will compete less with GCV for binding in the active-site. This appears to be the case in both cell lines tested for the Asn-125 mutant, and even in the HCT-116 cells expressing the Glu-125 mutant. The GCV metabolism properties and mechanistic aspects of GCV cell killing by the Asn-125 and Glu-125 mutants in the HCT-116 cells are further evaluated. These types of HSV-1 TK mutants described herein will allow the evaluation of whether the TK/TKMP activities of HSV-1 TK cause any cellular problems related to altered nucleotide metabolism and pool sizes. This could be especially important in the cancer gene therapy trials for myeloma (34) and leukemia (35) that administer HSV-1 TK-expressing T-lymphocytes to patients for immune protection and surveillance following bone marrow transplants. HSV-1 TK acts as a safety gene in these studies to allow termination of the treatment via GCV if graph-versus-host disease develops, thus use of an HSV-1 TK that is predominantly a GCV kinase could prove to be safer and more effective. Efforts to characterize the expression and metabolism of GCV in T-lymphocytes expressing Glu-125 and Asn-125 HSV-1 TKs are currently in progress.

The following references were cited herein:
1. Whitley, R. J., (1985) in *The Herpesviruses* (Roizman, B. and Lopez, C., eds) Vol. 4, 339–369, Plenum Press, New York.
2. Machida, H. (1986) *Antimicrob. Agents Chemo.* 29, 524–526.
3. Freeman, et al., (1996). *Sem. Onocol.*, 23, 31–45.
4. Tiberghien, P. (1994) *J. Leuk. Biol.*, 56, 203–209.
5. Elion, et al., (1977) *Proc. Nat. Acad. Sci. USA* 74, 5716–5720.
6. Kit, et al., (1974) *Int. J. Cancer* 13, 203–218.
7. Chen, et al., (1978) *J. Biol. Chem.* 253, 1325–1327.
8. Chen, et al., (1979) *J. Biol. Chem.*, 254, 10747–10753.
9. Mao, et al., (1995) *J. Biol. Chem.*, 270, 13660–13664.
10. Rechtin, et al., (1996) *Anal Biochem.*, 237, 135–140.
11. Maga, et al., (1994) *Biochem. J.*, 302, 279–282.
12. Rechtin, et al., (1995) *J. Biol. Chem.*, 270, 7055–7060.
13. Brown, et al., (1995) *Nature Struct. Biol.*, 2, 876–881.
14. Wild, et al., (1997) *Protein Sci.*, 6, 2097–2100.
15. Champness, et al., (1998) *Proteins Struct. Func. Genet.*, 82, 350–361.
16. Bennettt, et al., (1999) *FEBS Lett.*, 443, 121–125.
17. Kussmann-Gerber, et al., (1998) *Eur. J. Biochem.*, 255, 472–481.
18. Vieira, et al., (1987) *Meth. Enzymol.*, 153, 3–11.
19. Sayers, et al., (1992) *BioTechniques*, 13, 592–596.
20. Studier, et al., (1990) *Meth. Enzymol.* 185, 60–89.
21. Drake, et al., (1997) *Antiviral Res*, 35, 177–185.
22. Pastuszak, et al., (1996) *J. Biol. Chem.*, 271, 20776–20782.
23. Radominska, et al., (1993) *Meth. Enzymol.*, 230, 330–339.
24. McMasters, et al., (1998) *Human Gene Ther*, 9, 2253–2261.
25. Alley, et al., (1988) *Cancer Res.* 48, 589–601.
26. Drake, et al., (1999) *J. Biol. Chem.*,
27. Dube, et al., (1991) *Biochemistry* 30, 11760–11767.
28. Black, et al., (1993) *Biochemistry* 32, 11618–11626.
29. Black, et al., (1996) *Proc. Nat. Acad. Sci. USA*, 93, 3525–3529.
30. Chen, et al., (1995) *Human Gene Ther.*, 6, 1467–1476.
31. Ishii-Morita, et al., (1997) *Gene Ther.*, 4, 244–251
32. Kim, et al., (1999) *Cancer Gene Ther.*, In press.
33. Boucher, et al., (1998) *Human Gene Ther.*, 9, 801–814.
34. Munshi, et al., (1997) *Blood*, 89, 1334–1340.
35. Bonini, et al., (1997) *Science*, 276, 1719–1724.
36. Rubsam, et al., (1998) *Cancer Res.*, 58, 3873–3882.
37. Wei, et al., (1998) *Exp. Cell Res.*, 241, 66–75.
38. Halloran, et al., (1998) *Cancer Res.*, 58, 3855–3865.
39. Denning, et al., (1997) *Hum. Gene Ther.*, 8, 1825–1835.
40. Hamel, et al., (1996) *Cancer Res.*, 56, 2697–2702.
41. Rudel, et al., (1997). *Science* 276, 1571–1574.
42. Thornberry, et al., (1998) *Science* 281, 1312–1316.
43. Van Berkel et al., (1991) *Targeted Diagnosis and Therapy* 5: 225–249.
44. Allen, (1989) Liposomes in the Therapy of Infectious Diseases and Cancer, 405–415.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A vector comprising a DNA sequence encoding a mutant herpes simplex virus type 1 thymidine kinase protein, wherein said mutant protein has a non-glutamine residue at amino acid position 125 of wild type herpes simplex virus type 1 thymidine kinase protein, wherein said vector is capable of replication in a host and comprises, in operable linkage:

a) optionally, an origin of replication;
   b) a promoter; and
   c) a DNA sequence encoding said mutant protein.

2. The vector of claim 1, wherein said vector is selected from the group consisting of a retroviral vector, an adenoviral vector, an adeno-associated viral vector, a herpes vector, a viral vector and a plasmid.

3. An isolated host cell transfected with the vector of claim 1.

4. The host cell of claim 3, wherein said cell is selected from the group consisting of bacterial cells, mammalian cells and insect cells.

5. The vector of claim 1, wherein said non-glutamine residue is glutamic acid, aspartic acid or asparagine.

* * * * *